(12) United States Patent
Tanha

(10) Patent No.: US 11,993,643 B2
(45) Date of Patent: May 28, 2024

(54) METHOD FOR ISOLATION OF SOLUBLE POLYPEPTIDES

(71) Applicant: National Research Council of Canada, Ottawa (CA)

(72) Inventor: Jamshid Tanha, Orleans (CA)

(73) Assignee: NATIONAL RESEARCH COUNCIL OF CANADA, Ottawa (CA)

(*) Notice: Subject to any disclaimer, the term of this patent is extended or adjusted under 35 U.S.C. 154(b) by 386 days.

(21) Appl. No.: 17/372,966

(22) Filed: Jul. 12, 2021

(65) Prior Publication Data

US 2022/0017603 A1    Jan. 20, 2022

Related U.S. Application Data

(62) Division of application No. 16/210,621, filed on Dec. 5, 2018, now Pat. No. 11,091,536, which is a division of application No. 14/851,641, filed on Sep. 11, 2015, now Pat. No. 10,150,807, which is a division of application No. 13/656,099, filed on Oct. 19, 2012, now abandoned, which is a division of application No. 11/887,113, filed as application No. PCT/CA2006/000451 on Mar. 24, 2006, now Pat. No. 8,293,233.

(60) Provisional application No. 60/664,954, filed on Mar. 25, 2005.

(51) Int. Cl.
| | | |
|---|---|---|
| *C07K 16/00* | (2006.01) | |
| *C07K 16/12* | (2006.01) | |
| *C12N 15/10* | (2006.01) | |
| *G01N 33/68* | (2006.01) | |

(52) U.S. Cl.
CPC ........ *C07K 16/005* (2013.01); *C07K 16/1271* (2013.01); *C07K 16/1282* (2013.01); *C12N 15/1037* (2013.01); *G01N 33/6845* (2013.01); *C07K 2317/21* (2013.01); *C07K 2317/56* (2013.01); *C07K 2317/92* (2013.01); *C07K 2317/94* (2013.01)

(58) Field of Classification Search
CPC ............ C07K 16/005; C07K 2317/567; C12N 15/1037
USPC ............................................ 424/133.1; 435/5
See application file for complete search history.

(56) References Cited

U.S. PATENT DOCUMENTS

| | | | |
|---|---|---|---|
| 5,585,089 A | 12/1996 | Queen et al. | |
| 5,627,052 A | 5/1997 | Schrader | |
| 5,821,123 A | 10/1998 | Studnicka | |
| 8,293,233 B2 * | 10/2012 | Tanha | G01N 33/6845 435/5 |
| 2003/0028009 A1 | 2/2003 | Huse | |
| 2003/0059937 A1 | 3/2003 | Ruben et al. | |
| 2011/0269148 A1 | 11/2011 | Huang | |
| 2013/0142780 A1 | 6/2013 | Tanha | |

FOREIGN PATENT DOCUMENTS

| | | |
|---|---|---|
| EP | 1336848 A1 | 8/2003 |
| EP | 1429143 A1 | 6/2004 |
| EP | 1479694 | 11/2004 |
| JP | 2002-162398 A | 6/2002 |
| JP | 2008-536490 A | 9/2008 |
| WO | WO 98/01581 | 1/1998 |
| WO | WO 99/01556 | 1/1999 |
| WO | WO 00/61635 | 10/2000 |
| WO | WO 00/69914 | 11/2000 |
| WO | WO 2000/069914 | 11/2000 |
| WO | WO 01/72846 | 10/2001 |
| WO | WO 02/051870 | 7/2002 |
| WO | WO 2002/059340 | 8/2002 |

(Continued)

OTHER PUBLICATIONS

Kim et al (J Biol Chem Nov. 2023;299(11):105278. doi: 10.1016/j.jbc.2023.105278. Epub Sep. 22, 2023).*
Henry et al (Mol Immunol Oct. 2017:90: 190-196. doi: 10.1016/j.molimm.2017.07.006. Epub Aug. 15, 2017).*
European Search Report relating to European Patent Application No. 10 19 0165, dated Apr. 27, 2011.
European Search Report relating to European Patent Application No. 10 19 0246, dated Apr. 19, 2011.
European Search Report relating to European Patent Application No. 10 19 0237, dated May 17, 2011.
European Search Report relating to European Patent Application No. 10 19 0232, dated Mar. 22, 2011.
European Search Report relating to European Patent Application No. 10 19 0222, dated Mar. 22, 2011.
European Search Report relating to European Patent Application No. 10 19 0082, dated Mar. 22, 2011.

(Continued)

*Primary Examiner* — Lynn A Bristol
(74) *Attorney, Agent, or Firm* — CASSAN MACLEAN IP AGENCY INC.

(57) ABSTRACT

Polypeptides with biophysical properties such as solubility, stability, high expression, monomericity, binding specificity or non-aggregation, including monomeric human heavy and light chain variable domains ($V_H$s and $V_L$s), are identified using a high throughput method for screening polypeptides, comprising the steps of obtaining a phage display library, allowing infection of a bacterial lawn by the library phage, and identifying phage which form larger than average plaques on the bacterial lawn. Sequences of monomeric human $V_H$s and $V_L$s are identified, which may be useful for immunotherapy or as diagnostic agents. Multimer complexes of human $V_H$s and $V_L$s are also identified. The $V_H$s and $V_L$s identified may be used to create further libraries for identifying additional polypeptides. Further, the $V_H$s and $V_L$s may be subjected to DNA shuffling to select for improved biophysical properties.

14 Claims, 14 Drawing Sheets

Figure 1:
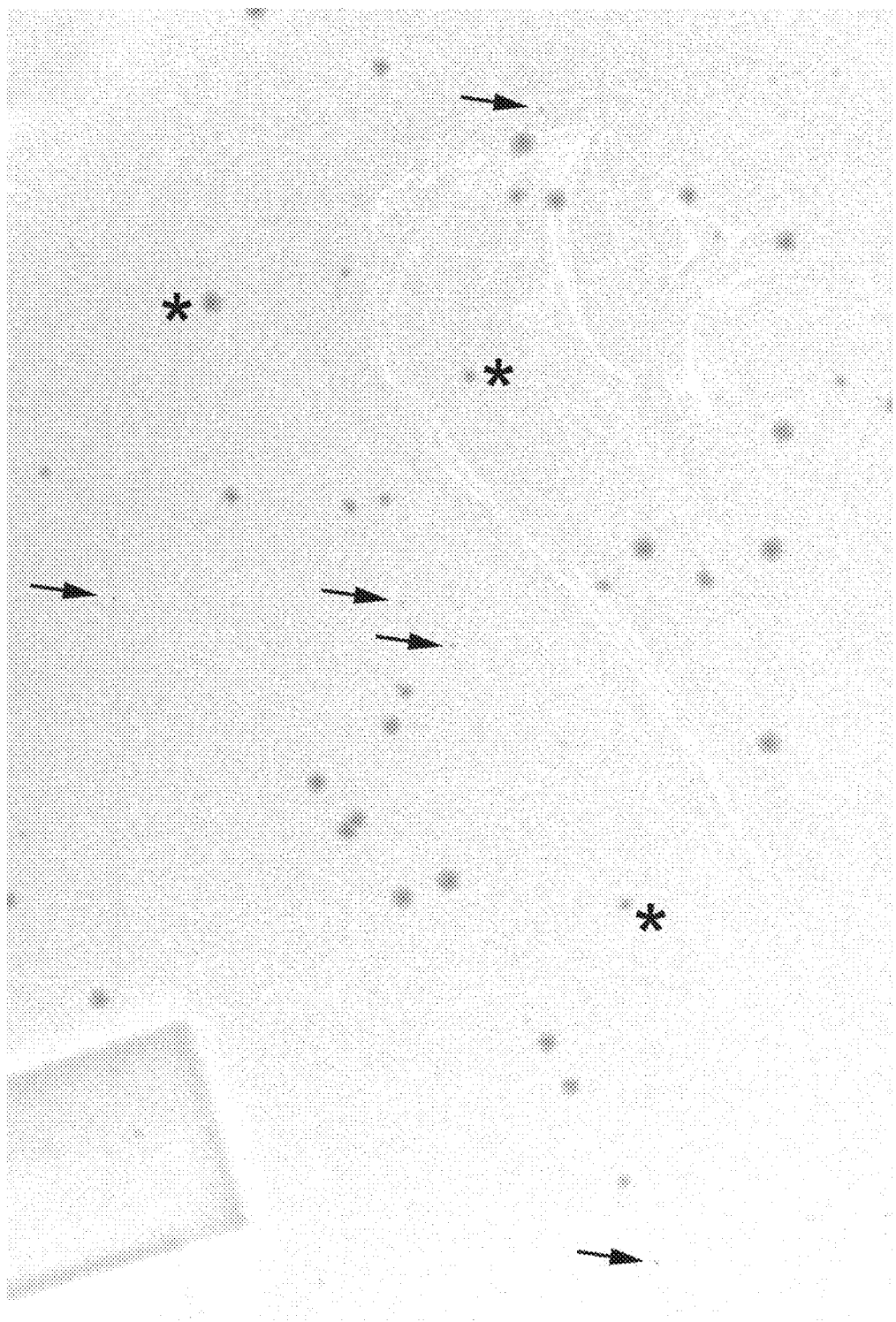
Figure 3A:
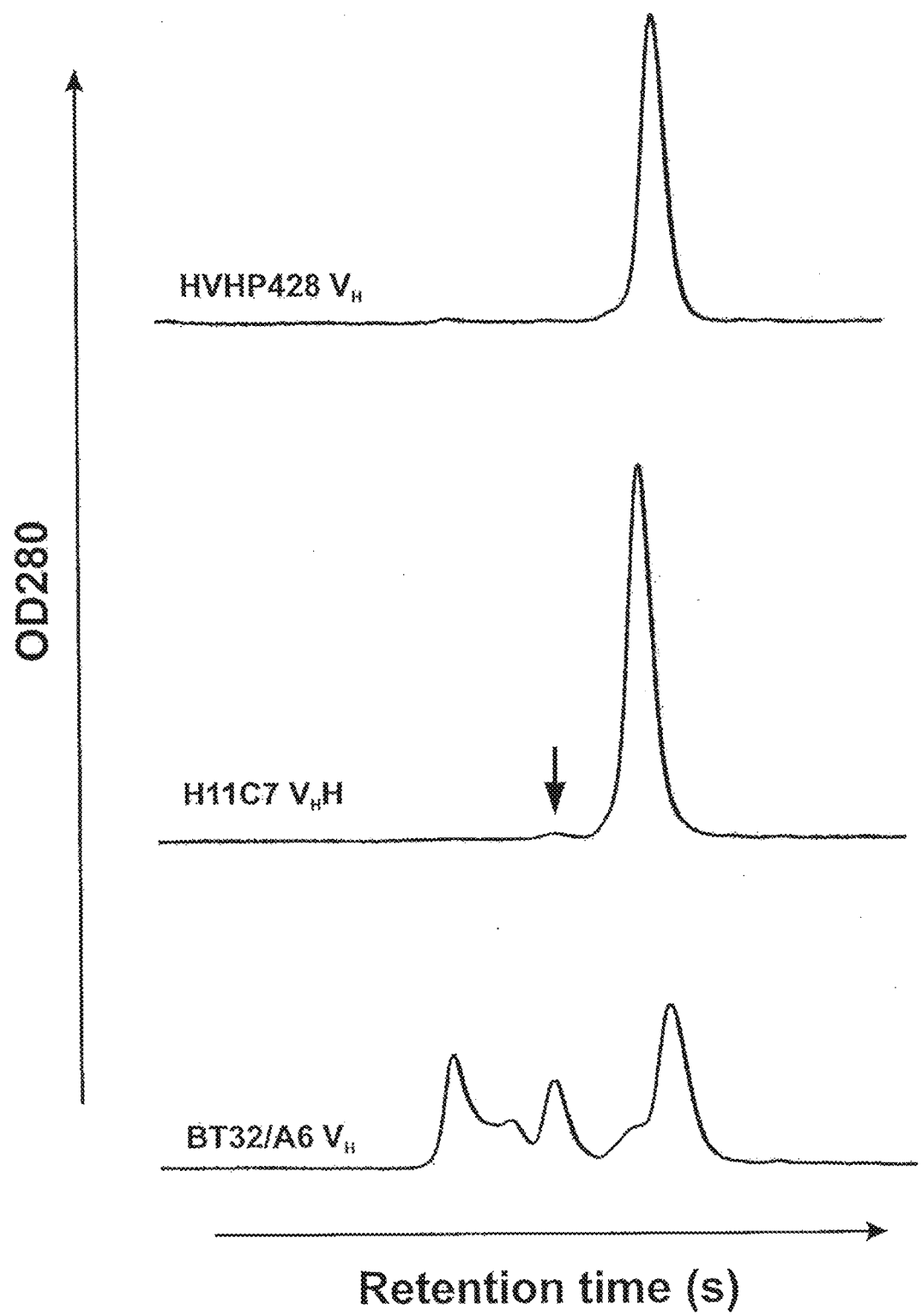
Figure 3B:
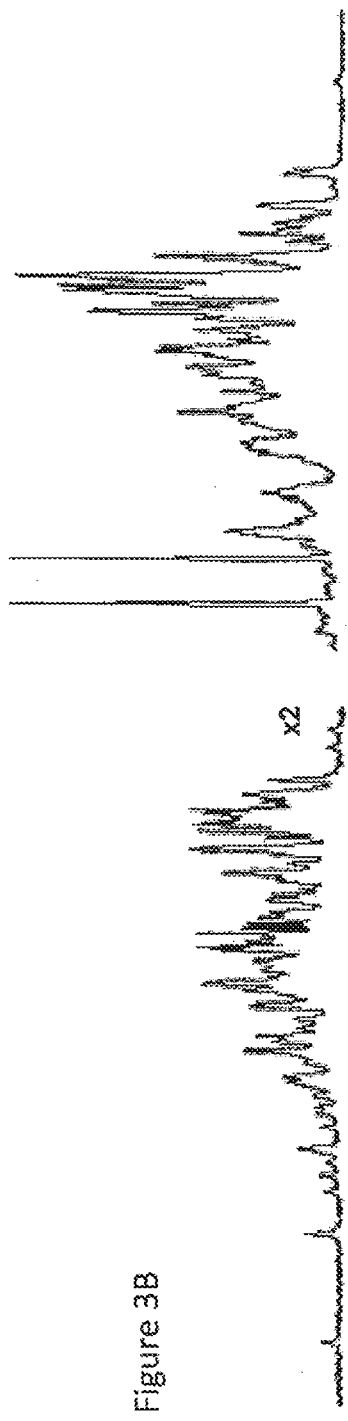
Figure 3C:
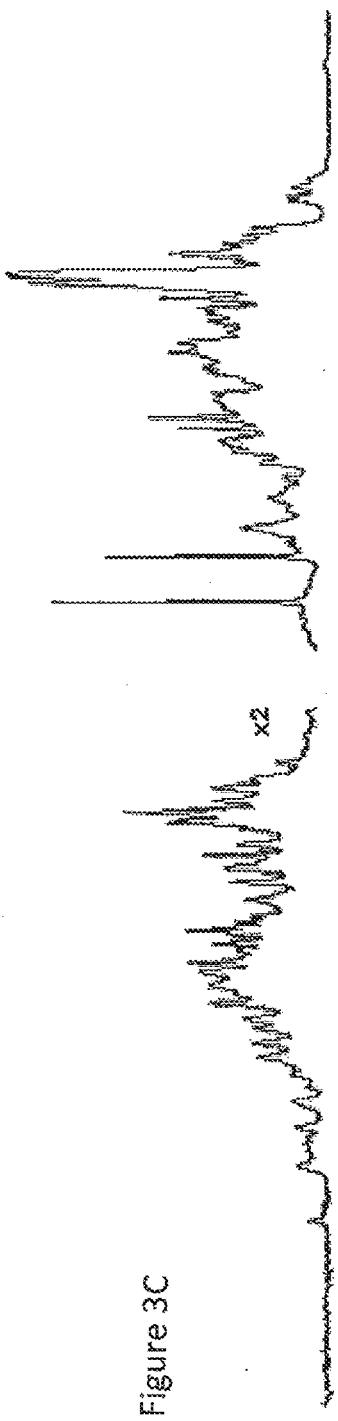
Figure 3D:
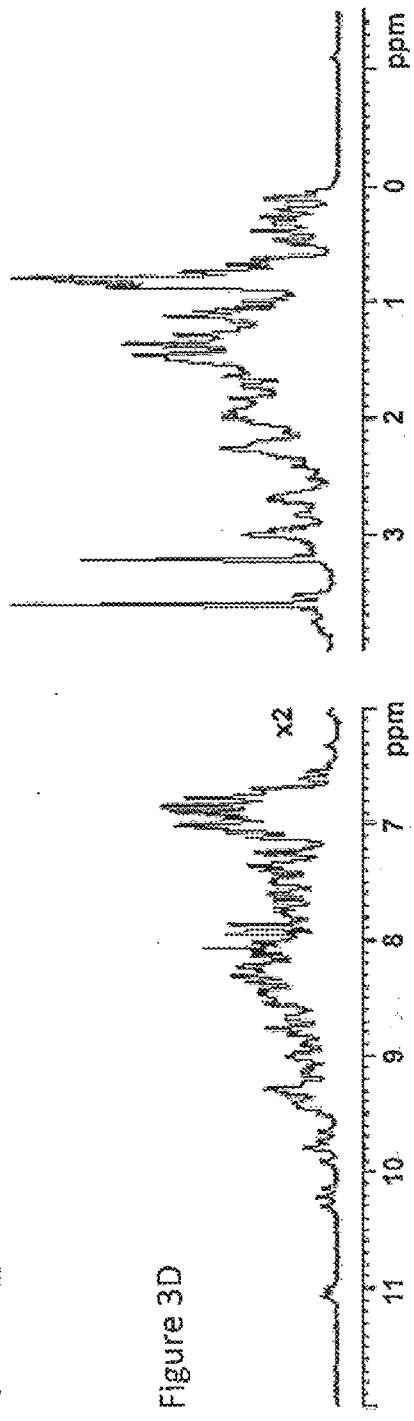

Specification includes a Sequence Listing.

(56) References Cited

FOREIGN PATENT DOCUMENTS

| WO | 2002/093519 A2 | 11/2002 |
|---|---|---|
| WO | WO 02/093519 | 11/2002 |
| WO | 2003/014960 | 2/2003 |
| WO | 2003/014960 A2 | 2/2003 |
| WO | 2003/0059937 A1 | 3/2003 |
| WO | 2003/070752 A2 | 8/2003 |
| WO | WO 2003/070752 | 8/2003 |
| WO | WO 2003/097697 | 11/2003 |
| WO | WO 03/104425 | 12/2003 |
| WO | WO 2003/102136 | 12/2003 |
| WO | 2004/003019 | 1/2004 |
| WO | WO 2004/005890 | 1/2004 |
| WO | WO 2004/046186 | 6/2004 |
| WO | WO 2004/046188 | 6/2004 |
| WO | WO 2004/083249 | 9/2004 |
| WO | WO 01/72771 | 10/2004 |
| WO | 2004/083249 A2 | 11/2004 |
| WO | WO 2005/016236 | 2/2005 |
| WO | WO 2005/023872 | 3/2005 |
| WO | WO 2005/042774 | 5/2005 |
| WO | 2005/094879 | 10/2005 |
| WO | 2005/094879 A2 | 10/2005 |
| WO | WO 2005/094879 | 10/2005 |
| WO | WO 2006/020706 | 2/2006 |
| WO | WO 01/87337 | 11/2011 |
| WO | 2012/100343 | 8/2012 |

OTHER PUBLICATIONS

European Search Report relating to European Patent Application No. 10 19 0248, dated Apr. 19, 2011.
European Search Report relating to European Patent Application No. 10 19 0249, dated May 18, 2011.
European Search Report relating to European Patent Application No. 10 19 0205, dated May 18, 2011.
European Search Report relating to European Patent Application No. 10 19 0180, dated Apr. 27, 2011.
Supplemental European Search Report relating to European Patent Application No. 06 72 1715, dated Aug. 4, 2008.
Office Action issued in European Patent Application No. 06 72 1715, dated Nov. 6, 2008.
Office Action issued in European Patent Application No. 06 72 1715, dated Feb. 10, 2009.
Office Action issued in European Patent Application No. 06 72 1715, dated Sep. 2, 2009.
Office Action issued in European Patent Application No. 06 72 1715, dated Apr. 21, 2010.
Office Action issued in Australian Patent Application No. 2006227536, dated Jul. 1, 2010.
Office Action issued in Australian Patent Application No. 2006227536, dated Apr. 5, 2011.
Notice of Allowance issued in European Patent Application No. 06 72 1715, dated May 26, 2011.
Notice of Acceptance issued in Australian Patent Application No. 2006227536, dated Jul. 27, 2011.
Office Action issued in Japanese Patent Application No. 2008-502207, prepared on Jul. 26, 2011.
European Search Report relating to European Patent Application No. 10 19 0155, dated Jun. 21, 2011.
European Search Report relating to European Patent Application No. 10 19 0210, dated Jun. 17, 2011.
European Search Report relating to European Patent Application No. 10 19 0176, dated Jun. 17, 2011.
European Search Report relating to European Patent Application No. 10 19 0242, dated Jun. 20, 2011.
European Search Report relating to European Patent Application No. 10 19 0086, dated Aug. 29, 2011.
European Search Report relating to European Patent Application No. 10 19 0149, dated Jul. 13, 2011.
European Search Report relating to European Patent Application No. 10 19 0162, dated Sep. 19, 2011.
European Search Report relating to European Patent Application No. 10 19 0225, dated Sep. 6, 2011.
European Search Report relating to European Patent Application No. 10 19 0235, dated Jul. 28, 2011.
European Search Report relating to European Patent Application No. 10190143.7-2405 / 2374886 dated Oct. 24, 2011.
Office Action relating to Japan Patent Application No. 2008-502207 dated Dec. 9, 2011.
Tanha, Jamshid, et al., "Improving Solubility and Refolding Efficiency of Human VHS by a Novel Mutational Approach", Protein Engineering, Design & Selection vol. 19, No. 11, Published on-line Sep. 19, 2006, pp. 503-509.
European Search Report relating to European Patent Application No. 10190147.8-2405 / 2368995 dated Dec. 16, 2011.
Adderson, Elizabeth, et al., "The Human VH3B Gene Subfamily is Highly Polymorphic 1", The Journal of Immunology, vol. 151, No. 2, Jul. 15, 1993, pp. 800-809.
European Search Report relating to European Patent Application No. 10190173.4-2405 / 2371960 dated Dec. 13, 2011.
Huber, Christian, et al., "The Vx Genes of the L Regions and the Repertoire of Vx Gene Sequences in the Human Germ Line"; Eur. J. Immunol. 1993. 23, pp. 2868-2875.
XP-002664369; "Human Germline fragment for Immunoglobulin kappa light Chain (subgroup III variable region gene V (g)" Sequence Listing.
XP003004702; "A directory of human germ-line Vx segments reveals a strong bias in their usage", Eur. J. Immunol. 1994. 24: pp. 827-836; Box, Jonathan P.L.
European Search Report relating to European Patent Application No. 101901007.7-2405 / 2368992 dated Feb. 10, 2012.
European Search Report relating to European Patent Application No. 10190145.2-2405 / 2368994 dated Mar. 19, 2012.
European Search Report relating to European Patent Application No. 10190153.6-2405 / 2322622 dated Mar. 2, 2012.
European Search Report relating to European Patent Application No. 10190169.2-2405 / 2336326 dated Jan. 18, 2012.
European examination report relating to European Patent Application No. 10190177.5-2405 dated Mar. 5, 2012.
European examination report relating to European Patent Application No. 10190180.9-2405 dated Feb. 27, 2012.
European search report relating to European Patent Application No. 10190187.4-2405 / 2322624 dated Feb. 15, 2012.
European search report relating to European Patent Application No. 10190244.3-2405 / 2368997 dated Jan. 24, 2012.
European examination report relating to European Patent Application No. 10190246.8-2405 dated Feb. 27, 2012.
European search report relating to European Patent Application No. 10190247.6-2405 / 2330196 dated Mar. 15, 2012.
European examination report relating to Patent Application No. 10190249.2-2405 dated Feb. 27, 2012.
Liu, Ming-Fei, et al., "Characterization of Four Homologous L Chain Variable Region Genes that are Related to 6B6.6 Idiotype Postivie Human Rheumatoid Factor L Chains" The Journal of Immunology—vol. 142, pp. 688-694, No. 2, Jan. 15, 1989.
First Examination Report dated Jan. 8, 2015 for Australian Patent Application No. 2013204557.
First Examination Report dated Dec. 11, 2014 for Australian Patent Application No. 2013204599.
First Examination Report dated Dec. 11, 2014 for Australian Patent Application No. 2013204679.
First Examination Report dated Dec. 11, 2014 for Australian Patent Application No. 2013204720.
First Examination Report dated Jan. 8, 2015 for Australian Patent Application No. 2013204781.
First Examination Report dated Jan. 8, 2015 for Australian Patent Application No. 2013204822.
Soderlind et al., "Domain Libraries: Synthetic diversity for de novo design of antibody V-regions", Gene, 1995, vol. 160, pp. 269-272.
Lin et al., "Screening and Selection Methods for Large-Scale Analysis of Protein Function", Angew. Chem. Int. Ed., 2002, vol. 41, pp. 4402-4425.

(56) References Cited

OTHER PUBLICATIONS

Yau et al., "Emerging trends in the synthesis and improvement of hapten-specific recombitant antibodies", Biotechnology Advances, 2003, vol. 21, pp. 599-637.
English Translation of Office Action dated May 21, 2015 for Japanese Patent Application No. 2014-070227.
First Examination Report dated Jan. 8, 2015 for Australian Patent Application No. 2013204493.
First Examination Report dated Jan. 6, 2015 for Australian Patent Application No. 2013204578.
Office Action dated Oct. 1, 2013 in connection with Japanese Patent Application No. 2011-254988.
Holt et al., "Domain antibodies: proteins for therapy", Trends in Biotechnology, 203, vol. 21, No. 11, pp. 484-490.
Lin et al., "Screening and Selection Methods for Large-Scale Analysis of Protein Function", Agnew. Chem. Int. Ed., 2002, vol. 41, pp. 4402-4425.
Yau et al., "Emerging trends in the synthesis and improvement of hapten-specific recombinant antibodies", Biotechnology Advances, 2003, vol. 21, pp. 599-637.
Office Action dated Oct. 18, 2013 in connection with European Patent Application No. 10 190 143.
Office Action dated Nov. 6, 2013 in connection with European Patent Application No. 10 190 177.
Office Action dated Sep. 27, 2013 in connection with European Patent Application No. 10 190 225.
Office Action dated Oct. 23, 2013 in connection with European Patent Application No. 10 190 249.
Office Action dated Nov. 12, 2013 in connection with European Patent Application No. 10 190 242.
Office Action dated Sep. 27, 2013 in connection with European Patent Application No. 10 190 248.
Hussack et al., "AVL single-domain antibody library shows a high-propensity to yield non-aggregating binders", Protein Engineering, Design & Selection, 2012, vol. 25, No. 6, pp. 313-318.
Examination Report issued in European Patent Application No. 10 190 187.4, dated Jun. 25, 2013.
Examination Report issued in European Patent Application No. 10 190 155.1, dated Jul. 29, 2013.
Examination Report issued in European Patent Application No. 10 190 104.9, dated Jul. 26, 2013.
Examination Report issued in European Patent Application No. 10 190 086.8, dated Jul. 29, 2013.
Examination Report issued in European Patent Application No. 10 190 093.4, dated Jul. 29, 2013.
Arbabi-Ghahroudi M et al., "Aggregation-resistant VHs selected by in vitro evolution tend to have disulfide-bonded loops and acidic points", Protein Engineering, Design and Selection, Oxford Journal, London, vol. 22, No. 2, Jan. 1, 2009, pp. 59-66.
Examination Report issued in Australian Patent Application No. 2011247831, dated Jul. 1, 2013.
Examiner's Report issued in European Patent Application No. 10190086.8, dated Jan. 8, 2013.
Examiner's Report issued in European Patent Application No. 10190089.2, dated Jan. 8, 2013.
Examiner's Report issued in European Patent Application No. 10190104.9, dated Dec. 14, 2012.
Examiner's Report issued in European Patent Application No. 10190145.2, dated Nov. 26, 2012.
Examiner's Report issued in European Patent Application No. 10190155.1, dated Jan. 9, 2013.
Examiner's Report issued in European Patent Application No. 10190187.4, dated Nov. 5, 2012.
Examiner's Report issued in European Patent Application No. 10190215.3, dated Dec. 11, 2012.
Examiner's Report issued in European Patent Application No. 10190225.2, dated Jan. 30, 3013.
Examiner's Report issued in European Patent Application No. 10190248.4, dated Jan. 30, 2013.

Examiner's Report relating to European Patent Application No. 10 190 237.7 dated Aug. 10, 2012.
Examiner's Report relating to European Patent Application No. 10 190 242.7 dated Aug. 16, 2012.
Examiner's Report relating to European Patent Application No. 10 190 246.8 dated Jul. 25, 2012.
Examiner's Report relating to European Patent Application No. 10 190 249.2 dated Jul. 25, 202.
Ichiyoshi, Yuji et al.; "A Human Anti-Insulin IgG Autoantibody Apparently Arises Through Clonal Selection from an Insulin-Specific "Germ-Line" Natural Antibody Template. Analysis by V Gene Segment Reassortment and Site-Directed Mutagenesis, " The Journal of Immunology, vol. 1654, No. 1, Jan. 1, 1995, pp. 226-238.
Examiner's Report relating to Canadian Patent Application No. 2,602,028 dated Jul. 19, 2012.
European Search Report relating to European Patent Application No. 101901007.7 dated Feb. 10, 2012.
European Search Report relating to European Patent Application No. 10 19 0089, dated Apr. 19, 2011.
European Search Report relating to European Patent Application No. 10 19 0177, dated May 18, 2011.
European Search Report relating to European Patent Application No. 10 19 0160, dated Mar. 31. 2011.
Examiner's Report issued in Canadian Patent Application No. 2,602,028 dated May 17, 2013.
Examiner's Report issued in European Patent Application No. 10190160.1 dated Apr. 19, 2013.
Examiner's Report issued in European Patent Application No. 1019014.3 dated Mar. 5, 2013.
Examiner's Report issued in European Patent Application No. 10190232.8 dated Apr. 23, 2013.
Examiner's Report issued in European Patent Application No. 10190236.9 dated Apr. 2, 2013.
Examiner's Report issued in European Patent Application No. 10190237.7 dated Apr. 2, 2013.
Examiner's Report issued in European Patent Application No. 10190242.7 dated Apr. 4, 2013.
Examiner's Report issued in European Patent Application No. 10190249.2 dated Mar. 14, 2013.
Examiner's Report dated Nov. 6, 2015 issued in connection with Canadian Patent Application No. 2,868,781.
Examiner's Report dated Nov. 6, 2015 issued in connection with Canadian Patent Application No. 2,873,939.
Examiner's Report dated Nov. 13, 2015 issued in connection with Canadian Patent Application No. 2,868,865.
Examiner's Report dated Nov. 16, 2015 issued in connection with Canadian Patent Application No. 2,868,774.
Examiner's Report dated Nov. 16, 2015 issued in connection with Canadian Patent Application No. 2,873,899.
Examiner's Report dated Nov. 13, 2015 issued in connection with Canadian Patent Application No. 2,868,867.
Examiner's Report dated Nov. 13, 2015 issued in connection with Canadian Patent Application No. 2,873,906.
Kobayashi et al., "Two-Step in Vitro Antibody Affinity Maturation Enables Estradiol-17β Assays with More than 10-Fold Higher Sensitivity", Anal. Chem., 2010, vol. 82, pp. 1027-1038.
Kim et al., "Improvement of anti-Burkholderia mouse monoclonal antibody from various phage-displayed single-chain antibody libraries", J. Immunol. Methods, 2011, vol. 372, No. 1-2, pp. 146-161.
Office Action issued in respect of Japanese Patent Application No. 2015-208267 dated Oct. 25, 2016.
Office Action issued in respect of Japanese Patent Application No. 2015-208269 dated Oct. 25, 2016.
Examiner's Report issued in respect of Canadian Patent Application No. 2,873,906 dated Sep. 16, 2016.
Examiner's Report issued in respect of Canadian Patent Application No. 2,873,899 dated Sep. 19, 2016.
Examiner's Report issued in respect of Canadian Patent Application No. 2,873,939 dated Sep. 13, 2016.
Examiner's Report issued in respect of Canadian Patent Application No. 2,868,865 dated Sep. 15, 2016.
Examiner's Report issued in respect of Canadian Patent Application No. 2,868,867 dated Sep. 19, 2016.

(56) References Cited

OTHER PUBLICATIONS

Examiner's Report issued in respect of Canadian Patent Application No. 2,868,774 dated Sep. 15, 2016.
Examiner's Report issued in respect of Canadian Patent Application No. 2,868,781 dated Sep. 13, 2016.
Office Action dated Aug. 8, 2017 for Japanese Patent Application No. 2015-208267.
Examiner's Report dated Oct. 17, 2017 for Canadian Patent Application No. 2,873,899.
Examiner's Report dated Oct. 17, 2017 for Canadian Patent Application No. 2,873,906.
Examiner's Report dated Oct. 17, 2017 for Canadian Patent Application No. 2,873,939.
Matsuda, Fumihiko, et al., "Structure and physical map of 64 variable segments in the 3' 0.8-megabase region of the human immunoglobulin heavy-chain locus" Article pp. 88-94.
Pargent, Walter, et al., "The human immunoglobulin x locus. Characterization of the duplicted O regions*"; Eur. J. Immunol. 1991. 21 pp. 1821-1827.
Pech, Michael, et al., Immunoglobulin genes of different subgroups are interdigitated within the Vk locus; Nucleic Acids Research, vol. 12 No. 23, Dec. 11, 1984.
XP-002666904; *H. sapiens* gene for IG kappa light chain variable region "02".
Examiner's Report related to Australian Patent Application No. 2011247831 dated May 8, 2012.
Bentley, David L. et al., Evolution of Immunoglobulin V. Genes: Evidence Indicating That Recently Duplicated Human V Sequences have diverged by Gene Conversion; Cell. Vol. 32, pp. 181-189, Jan. 1983.
Berman, Jeffrey E. et al., Content and organization of human Ig VH locus: definition of three new VH families and linkage to the Ig CH locus; The EMBO Journal, vol. 7, No. 3, pp. 727-738, 1988.
Chen, Pojen, P. et al., "Genetic basis for the cross-reactive idiotypes on the light chains of human IgM anti-IgG autoantibodies"; Proc. Natl. Acad. Sci, USA, vol. 83, pp. 8318-8322, Nov. 1986.
EMBL Database DQ101030; "Homosapiens isolate N16K immunoglobulin kappa light chain variable region".
EMBL Database X12686; "Human germline immunoglobulin kappa light chain V-segment A27".
EMBL Database X72808; *H. sapiens* Ig germline kappa-chain gene variable region (A30).
Examiner's Report relating to European Patent Application No. 10 190 089.2-2405 dated Jun. 6, 2012.
Examiner's Report relating to European Patent Application No. 10 190 086.8-2405 dated Jun. 5, 2012.
European search report relating to European Patent Application No. 10 190 091.8-2405 / 2338999 dated Apr. 20, 2012.
European search report relating to European Patent Application No. 10 190 102.3-2405 / 2368993 dated May 11, 2012.
Examiner's report relating to European Patent Application No. 10 190 149.4-2405 dated Jun. 5, 2012.
Examiner's report relating to European Patent Application No. 10 190 155.1-2405 dated Jun. 5, 2012.
Examiner's report relating to European Patent Application No. 10 190 160.1-2405 dated Apr. 2, 2012.
European search report relating to European Patent Application No. 10 190 162.7-2405 dated May 11, 2012.
Examiner's report relating to European Patent Application No. 10 190 165.0-2405 dated Apr. 4, 2012.
European search report relating to European Patent Application No. 10 190 215.3-2405 / 2330195 dated Apr. 20, 2012.
Examiner's Report relating to European Patent Application No. 190 232.8-2405 dated Jun. 11, 2012.
Examiner's Report relating to European Patent Application No. 190 235.1-2405 dated Jun. 4, 2012.
Examiner's Report relating to European Patent Application No. 190 236.9-2405 dated Apr. 3, 2012.
Examiner's Report relating to European Patent Application No. 190 237.7-2405 dated Apr. 2, 2012.
European search report relating to European Patent Application No. 10 190 240.1-2405 / 2377936 dated May 15, 2012.
Examiner's Report relating to European Patent Application No. 10 190 242.7-2405 dated Apr. 3, 2012.
Examiner's Report relating to European Patent Application No. 10 190 248.4-2405 dated Jun. 8, 2012.
Huber, Christian, et al., "The Vx genes of the L regions and the repertoire of Vx gene sequences in the human germ line"; Euro. J. Immunol. (1993) 23 pp. 2868-2875.
Stamatopoulos, Kostas, et al., "Immunoglobulin light chain repertoire in chronic lymphocyctic leukemia" Blood 2005 106; pp. 3575-3583; Prepublished online Aug. 2, 2005.
Straubinger, Bernhard, et al., "The Human VK Lobus Characterization of Duplicated Region Encoding 28 Different Immunoglobulin Genes"; J. Mol. Biol. (1988) 199 pp. 23-24.
Tomlinson, Ian M., et al., "The Repertoire of Human Germline VH Sequences Reveals about Fifty Groups of VH Segments with Different Hypervariable Loops"; J. Mol. Biol. (1992) 227, pp. 776-798.
Williams, Samuel C.; "Sequence and Evolution of the Human Germline VA Repertoire"; J. Mol. Biol. (1996) 264, pp. 220-232.
Examiner's Report relating to European Patent Application No. 10 190 225.2-2405 dated Jun. 8, 2012.
European search report relating to European Patent Application No. 10 190 201.3-2405 / 2374887 dated Jun. 19, 2012.
European search report relating to European Patent Application No. 10 190 093.4-2405 / 2368991 dated Jun. 25, 2012.
Examiner's Report relating to European Patent Application No. 10 190 143.7-2405—dated Jul. 23, 2012.
Examiner's Report relating to European Patent Application No. 10 190 147.8-2405 dated Aug. 2, 2012.
Examiner's Report relating to European patent Application No. 10 190 160.1-2405 dated Aug. 10, 2012.
Examiner's Report relating to European Patent Application No. 10 190 162.7-2405 dated Aug. 16, 2012.
Examiner's Report relating to European Patent Application No. 10 190 165.0-2405 dated Aug. 16, 2012.
Examiner's Report relating to European Patent Application No. 10 190 173.4-2045 dated Aug. 3, 2012.
Examiner's Report relating to European Patent Application No. 10 190 176.7-2405 dated Jul. 2, 2012.
Examiner's Report relating to European Patent Application No. 10 190 177.5-2405 dated Jul. 31, 2012.
Examiner's Report relating to European Patent Application No. 10 190 180.9-2045 dated Jul. 25, 2012.
European Search Report relating to European Patent Application No. 10 190 194.0-2405 / 2322621 dated Aug. 13, 2012.
Examiner's Report relating to European Patent Application No. 10 190 210.4-2405 dated Jul. 2, 2012.
Examiner's Report relating to European Patent Application No. 10 190 232.8-2405 dated Aug. 16, 2012.
Examiner's Report relating to European Patent Application No. 10 190 235.1-2405 dated Aug. 16, 2012.
Examiner's Report relating to European Patent Application No. 10 190 236.9-2405 dated Aug. 10, 2012.
To R et al. "Isolation of Monomeric Human VS by a Phage Selection" The Journal of Biological Chemistry, Dec. 16, 2005. vol. 280, No. 50, pp. 41395-41403.
O'Neil, K. et al. "Thermodynamic Genetics of The Folding of the B1 Immunoglobulin-Binding Doman From Streptococcal Protein G" Proteins: Structure, etc. 1995, vol. 21, pp. 11-21.
Jespers L. et al. "Aggregation-Resistant Domain Antibodies Selected on Phage by Heat Denaturation" Nature Biotechnology, Sep. 2004, vol. 22, No. 9, pp. 1161-1165.
Jung, S. et al. "Selection for Improved Protein Stability by Phage Display" Journal of Molecular Biology, 1999, vol. 294, No. 1, pp. 163-180.
Hoess, R.H., "Protein Design and Phage Display", Chemical Reviews, ACS, Washington, D.C. US, vol. 101, No. 1 10, Aug. 18, 2001, pp. 3205-3218, ISSN: 0009-2665.

(56) References Cited

OTHER PUBLICATIONS

Proba, K. et al: "Antibody scFv Fragments without Disulfide bonds, made by molecular evolution", Journal of Molecular Biology, London, GB, vol. 275, No. 2, Jan. 16, 1998, pp. 245-243, ISSN: 0022-2836.
Song, et al. (Biochem Biophys Res Comm 268:390-394 (2000).
Wu, et al. Journal of Molecular Biology (1999) 294, pp. 151-162.
Ward, et al. (Nature 341: pp. 544-546 (1989).
Smith-Gill, et al. (Journal of Immunology 139: pp. 4135-4144 (1987).
Kumar, et al., Journal of Biological Chemistry, 275 pp. 35129-35136, (2000).
Casset, et al. (2003) BBRC 307, pp. 198-205.
Vajdos, et al. (2002) Journal of Molecular Biology, 320 pp. 415-428.
Holm, et al. (2007) Molecular Immonology, 44 pp. 1075-1084.
Chen, et al. Journal of Molecular Biology, (1999) 293, pp. 865-881.
Lederman, et al., Molecular Immunology 28 pp. 1171-1181, 1991.
Li, et al., Proc. Natl. Acad. Sci. USA 77 pp. 3211-3214, 1980.
Maccallum, et al., Journal of Molecular Biology (1996) 262 pp. 732-745.
Depascalis et al., The Journal of Immunology (2002) 169, pp. 3076-3084.
Bai, Y. and Feng, J. (2004). Selection of stably folded proteins by phage-display with proteolysis. Eur. J. Biochem. 271: pp. 1609-1614.
Davies, J. and Reichmann, L. (Feb. 21, 1994). Camelising human antibody fragments: NMR studies on VH domains. FEBS lett 339; pp. 284-290.
Davies, J. and Riechmann, L. (1995) "Antibody VH domains as small recognition units". Biotechnology N.Y. 13: pp. 475-479.
De Haard, H.J., Van Neer, N., Reurs, A., Hufton, S.E., Roovers, R.C., Henderikx, P., De Bruine, A.P., Arends, J.W., and Hoogenboom, H.R. (Jun. 25, 1999). A Large non-immunized human Fab Fragment phage library that permits rapid isolation and kinetic analysis of high affinity antibodies, Journal of Biological Chemistry, 274, pp. 18218-18230.
Deng, S.J.; Mackenzie, C.R., Hirama, T., Brousseau, R., Lowary, T.L., Young, N.M., Bundle, D.R. and Narang, S.A. (May 23, 1995). "Basis for selection of improved carbohydrate-binding single-chain antibodies from synthetic gene libraries". Proc. Natl. Acad. Sci. U.S.A. 92; pp. 4992-4996.
Forrer, B., Jung, S., and Pluckthun, A. (1999). Beyond binding: using phage display to select for structure, folding and enzymatic activity in proteins. Curr. Opin. Struct. Biol. 9: pp. 514-520.
Fournier, B. and Klier, A. (2004). Protein A gene expression is regulated by DNA supercoiling which is modified by the ArlS-ArlR two-component system of *Staphylococcus aureus*. Microbiology 150: pp. 3807-3819.
Hamers, C.C., Atarhouch, T., Muyldermans, S., Robinson, G., Hamers, C., Songa, E.B., Bendahman, N., and Hamers, R. (Jun. 3, 1993). "Naturally occurring antibodies devoid of light chains." Nature 363: pp. 446-448.
Jespers, L., Schod, O., James, L.C., Veprintsev, D., and Winter, G. (Apr. 2, 2004b). Crystal Structure of HEL4, a Soluble, Refoldable Human V (H) Single Domain with a Germ-line Scaffold .; Journal of Molecular Biology, 337, pp. 893-903.
Matsura, T., and Pluckthun, A., (Mar. 27, 2003). "Selection based on the folding properties of proteins with ribosome display". FEBS Lett. 539; pp. 24-28.
Muruganandam, A., Tanha, J., Narang, S., and Stanimirovic, D. (2002). "Selection of phage-displayed llama single-domain antibodies that transmigrate across human blood-brain barrier endothelium". FASEB J. 16: pp. 240-242.
Pace, C.N., Vajdos, F., Fee, L., Grimsley, G., and Gray, T. (1995). "How to measure and predict the molar absorption coefficient of a protein". Protein Sci: 4; pp. 2411-2423.
Ricci, S., Medaglini, D., Marcotte, H., Olsen, A., Pozzi, G., and Bjorck, L. (2001). "Immunoglobulin-binding domains of peptostreptococcal protein L enhance vaginal colonization of mice by *Streptococcus gordnii*." Microb. Pathog. 30: pp. 229-235.

Sblattero, D., and Bradbury, A. (1998). "A definitive set of oligonucleotide primers for amplifying human V regions". Immunotechnology. 3: pp. 271-278.
Tanha, J., Dubuc, G., Hirama, T., Narang, S.A. and MacKenzie, C.R., (May 1, 2002). "Selection by phage display of llama convention V (H) fragments with heavy chain antibody V (H) H properties". Journal of Immunology Methods 263: pp. 97-109.
Tanha, J., Muruganandam, A., and Stanimirovic, D., (2003), "Phage Display Technology for Identifying Specific Antigens on Brain Endothelial Cells". Method Mol. Med. 89: pp. 435-450.
Tanha, J., Xu, P., Chen, Z.G., Ni, F., Kaplan, H., Narang S.A., and Mackenzie, C.R. (Jul. 6, 2001). "Optimal design features of camelized human single-domain antibody libraries." Journal of Biological Chemistry 276: pp. 24774-24780.
Van Der Linden, R.H.; Frenken, L.G., De Geus, B., Harmsen, M.M., Ruuls, R.C., Stok, W., de Ron, L., Wilson, S., Davis, p. and Verrips, C.T. (Apr. 12, 1999). "Comparison of physical chemical properties of llama VHH antibody fragments and mouse monoclonal antibodies." Biochim. Biophys. Acta 1431: pp. 37-46.
Waldo, G.S. (2003). "Genetic screens and directed evolution for protein solubility". Curr. Opin. Chem. Biol. 7: pp. 33-38.
Ward, E.S., Gussow, D., Griffith, A.D., Jones, P.T., and Winter, G. (Oct. 12, 1989). Binding activities of a repertoire of single immunoglobulin variable domains secreted from *Escherichia coli* [see comments]. Nature 341: pp. 544-546.
Zhang, J.,; Li, Q., Nguyen, T.D., Tremblay, T.L., Stone, E., To, R., Kelly, J., and Mackensie, C.R. (7-30-3004). "A pentavalent single-domain antibody approach to tumor antigen discovery and the development of novel proteomics reagents." Journal of Molecular Biology 341: pp. 161-169.
Forrer, Patrick, et al., "Beyond Binding: using phage display to select for structure, folding and enzymatic activity in proteins", Structural Biolody 1 999, 9: pp. 514-520.
Filpula, D., "Antibody engineering and modification technologies", Biomolecular Engineering 24 (2007) pp. 201-215.
Jung, Sabine, et al., "Selection for Improved Protein Stability by Phage Display".
Hudson, P.J., et al., "High Avidity scFv Multimers; Diabodies and Triabodies", Journal of Immunological Methods, Elsevier Science Publishers B.V., Amsterdam, NL, vol. 231, No. 1-2, Dec. 10, 1999, pp. 177-189.
Wang, Xiang-Bin et al., "A New Approach for Rapidly Reshaping Single-Chain Antibody in Vitro by Combining DNA Shuffling with Ribosome Display", Journal of Biochemistry, Tokyo, vol. 136, No. 1, Jul. 2004, pp. 19-28.
Woern, A. et al., "Stability Engineering of Antibody Single-Chain Fv Fragments", Journal of Molecular Biology, London, GB, vol. 305, No. 5, Jan. 1, 2001, pp. 989-1010.
European Search Report relating to European Patent Application No. 10 19 0236, dated May 11, 2011.
Arbabi-Ghahroudi et al., "Selection of Non-aggregating VH Binders from Synthetic VH Phage-Display Libraries", Therapeutic Antibodies, pp. 187-216, 2009.
Henry et al., "Stability-Diversity Tradeoffs Impose Fundamental Constraints on Selection of Synthetic Human VH/VL Single-Domain Antibodies from In Vitro Display Libraries", Frontiers in Immunology, 8:1759, Dec. 2017.
Henry et al., "Performance Evaluation of Phage-Displayed Synthetic Human Single-Domain Antibody Libraries: A Retrospective Analysis", Journal of Immunological Methods 456:81-86, 2018, Epub Feb. 17, 2018.
Kim et al., "Solubility and Stability Engineering of Human VH Domains", Methods Mol. Biol., 911:355-372, 2012.
Office Action issued for Japanese Patent Application No. 2018-018992, dated Feb. 5, 2019.
Examiner's Report issued for Canadian Patent Application No. 2,873,899, dated Jul. 17, 2019.
Examiner's Report issued for Canadian Patent Application No. 2,873,906, dated Jul. 22, 2019.
Examiner's Report issued for Canadian Patent Application No. 2,873,939, dated Jul. 22, 2019.

* cited by examiner

Figure 2

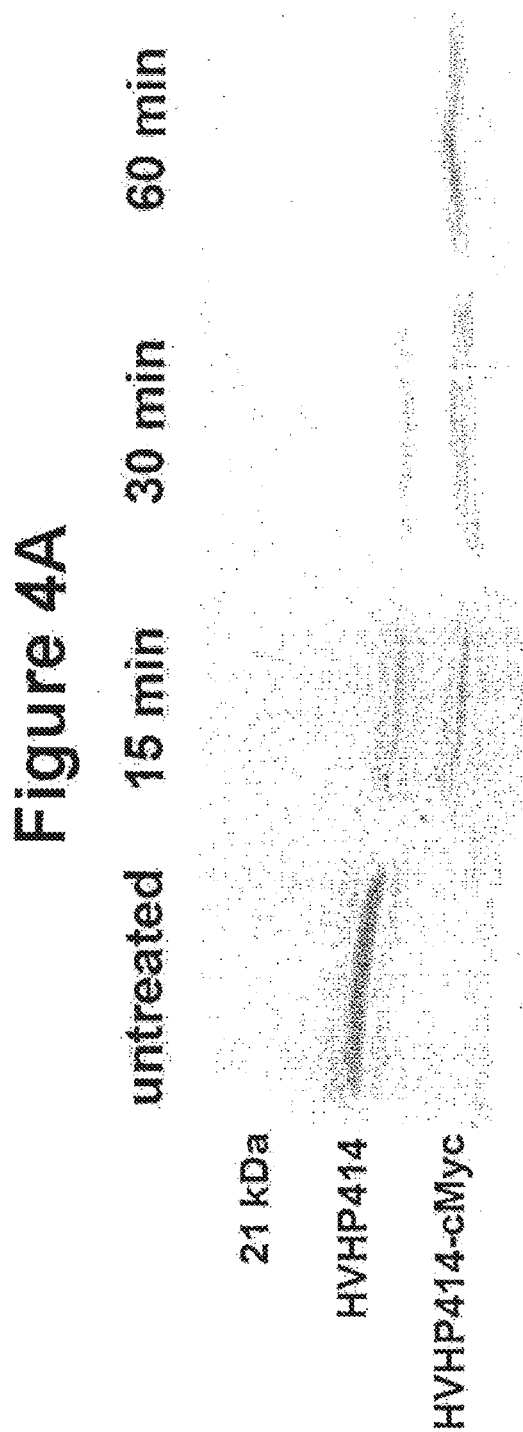

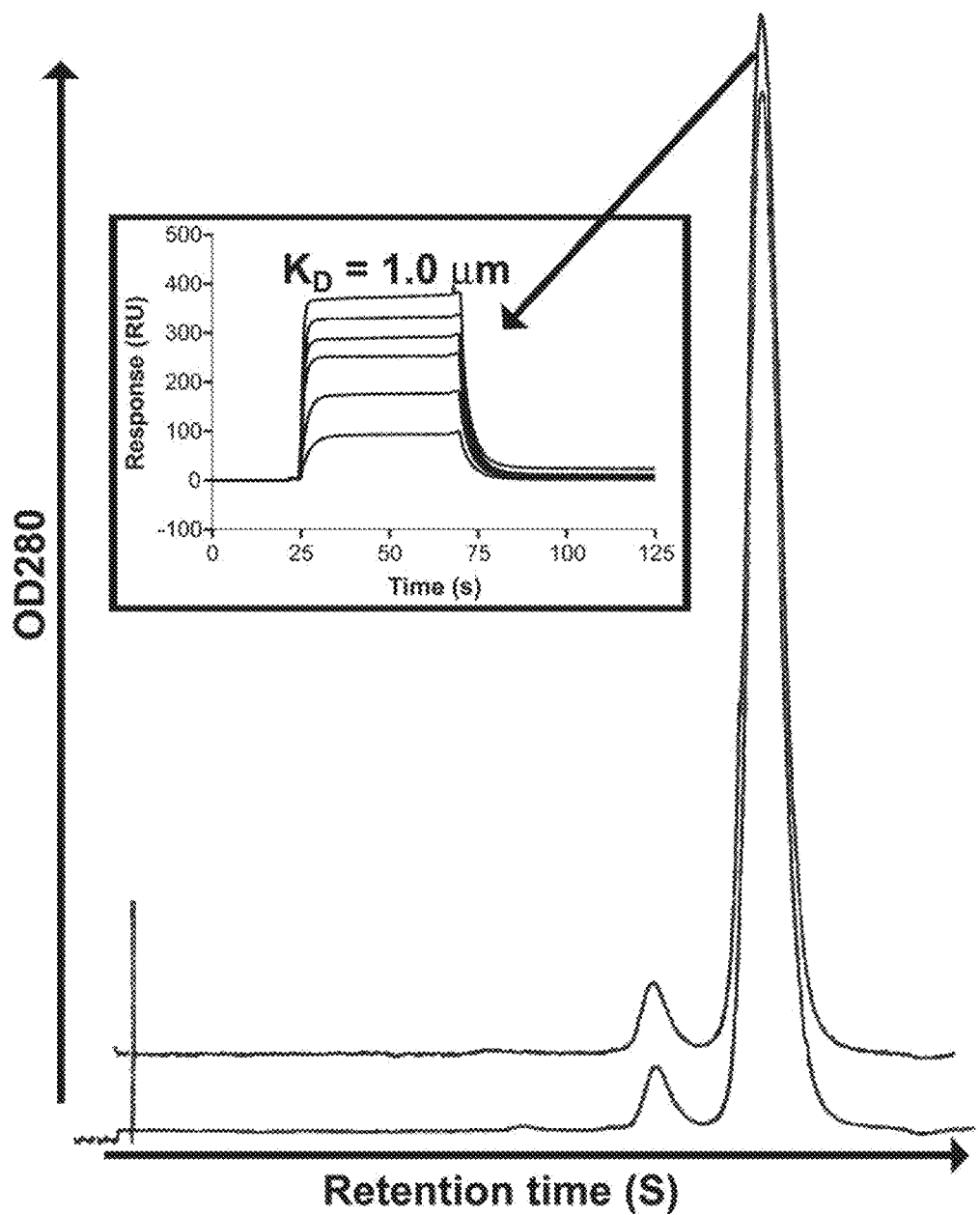

Figure 6

METHOD FOR ISOLATION OF SOLUBLE POLYPEPTIDES

This application is a division of U.S. patent application Ser. No. 16/210,621, which is a division of U.S. patent application Ser. No. 14/851,641, which is a division U.S. patent application Ser. No. 13/656,099, which is a division of U.S. patent application Ser. No. 11/887,113 issued as U.S. Pat. No. 8,293,233, which is a 371 of PCT Application No. PCT/CA2006/000451, which claims the benefit of U.S. Provisional Patent Application No. 60/664,954.

The sequence listing is provided herewith in electronic form under the file name 2012_12_06 sequence_listing.txt, created on Dec. 6, 2012, with a size of 56,279 bytes, and is hereby incorporated by reference.

FIELD OF THE INVENTION

This invention relates to the isolation, identification and manipulation of polypeptides, especially monomeric human antibody fragments.

BACKGROUND OF THE INVENTION

Antibodies in vertebrates are typically composed of paired heavy (H) and light (L) chains. The first domain of the combined H and L chains, the $V_H$ and $V_L$, are more variable in sequence, and this is the portion of the antibody that recognizes and binds to the antigen. The $V_H$ and $V_L$ domains recognize the antigen as a pair.

The immune repertoire of camelidae (camels, dromedaries and llamas) is unique in that it possesses unusual types of antibodies referred to as heavy-chain antibodies (Hamers, Casterman C. et al., 1993). These antibodies lack light chains and thus their combining sites consist of one domain, termed $V_HH$.

Recombinant $V_HH$ single-domain antibodies (sdAbs) provide several advantages over single-chain Fv (scFv) fragments derived from conventional four-chain antibodies. While sdAbs are comparable to their scFv counterparts in terms of affinity, they outperform scFvs in terms of solubility, stability, resistance to aggregation, refoldability, expression yield, and ease of DNA manipulation, library construction and 3-D structural determinations. Many of the aforementioned properties of $V_HH$ sdAbs are desired in applications involving antibodies.

However, the non-human nature of $V_HH$s limits their use in human immunotherapy due to immunogenicity. In this respect, human $V_H$ and $V_L$ sdAbs are ideal candidates for immunotherapy applications because they are expected to be least immunogenic.

Human $V_H$s and $V_L$s, however, are by and large prone to aggregation, a characteristic common to $V_H$s and $V_L$s derived from conventional antibodies (Davies, J. et al., 1994; Tanha, J. et al., 2001; Ward, E. S. et al., 1989). Thus, attempts have been made to obtain monomer human $V_H$s and $V_L$s suitable for antibody applications. Such $V_H$s and $V_L$s have also displayed other useful properties typical of $V_HH$s such as high expression yield, high refoldability and resistance to aggregation. Synthetic libraries built on these $V_H$s and $V_L$s as library scaffolds might serve as a promising source of therapeutic proteins.

Camelization as well as llamination which involves incorporating key solubility residues from camel and llama $V_HH$s, respectively, into human $V_H$s or $V_L$s have been employed to generate monomeric human $V_H$s and $V_L$s. Synthetic sdAb libraries constructed based on these $V_H$s and $V_L$s and generated by CDR randomization were shown to be functional in terms of yielding binders to various antigens (Davies, J. et al., 1995; Tanha, J. et al., 2001).

In another approach, fully human monomeric $V_H$s and $V_L$s were isolated from human synthetic $V_H$ and $V_L$ libraries without resorting to engineering of the sort mentioned above. In one experiment a monomeric human $V_H$, was discovered when a human $V_H$ library was panned against hen egg lysozyme (Jespers, L. et al., 2004b). More recently, a selection method based on reversible unfolding and affinity criteria yielded many monomeric $V_H$s from synthetic human $V_H$ libraries (Jespers, L. et al., 2004a). This finding underlined the fact that an appropriate selection method is key to efficient capturing of rare monomer human $V_H$s with desirable biophysical properties.

OBJECTS OF THE INVENTION

A first object of the invention is to provide a high throughput screening method for identifying polypeptides, especially antibody fragments, with improved biophysical properties, including solubility, high expression, and/or stability (such as high refolding after thermal denaturation, high resistance to chemical denaturant, and high resistance to proteases, in particular gastrointestinal proteases such as trypsin).

A second object of the invention is to provide a high throughput screening method for identifying monomeric human $V_H$s and $V_L$s.

A third object of the invention is to identify, isolate and characterize monomeric human $V_H$s and $V_L$s.

A fourth object of the invention is to construct and characterize multimers of antibody fragments, especially monomeric human $V_H$s and $V_L$s.

A fifth object of the invention is to construct display libraries from polypeptides, especially antibody fragments, and most especially monomeric human $V_H$s and $V_L$s.

A sixth object of the invention is to provide a DNA shuffling method for producing polypeptides, especially antibody fragments, and most especially monomeric human $V_H$s and $V_L$s with improved biophysical properties.

SUMMARY OF THE INVENTION

A method is provided for isolating polypeptides, preferably antibody fragments, and most preferably human $V_H$s and $V_L$s with desirable biophysical properties (solubility, stability, high expression, monomericity, non-aggregation, binding specificity). The method includes the steps of obtaining a phage display library capable of expressing a variety of polypeptide sequences, allowing infection of a bacterial lawn by the library phage, and identifying phage which form larger than average plaques on the bacterial lawn. The phage are then isolated, and steps are taken to sequence or otherwise characterize the polypeptide sequences.

The invention also provides for polypeptides, especially monomeric human $V_H$s and $V_L$s, identified by the above method, which may be useful for immunotherapy, and/or as diagnostic or detection agents. The monomeric human $V_H$s and $V_L$s may also be combined to form dimers, trimers, pentamers or other multimers, which may be useful for immunotherapy and/or as diagnostic or detection agents.

The polypeptides identified by the above method, including human $V_H$s and $V_L$s, can be manipulated by methods such as DNA shuffling to select for improved biophysical properties such as solubility, stability, monomericity, high expressibility, binding specificity and human origin.

The polypeptides identified by the above method, including human $V_H$s and $V_L$s, may also be used to generate further display libraries, which can then in turn be used to isolate further polypeptides by the above method.

In a first aspect, the present invention provides a method of identifying target polypeptides, comprising a) obtaining a phage display library capable of expressing a variety of polypeptide sequences, b) allowing infection of a bacterial lawn by the library phage and c) identifying phage which form larger than average plaques on the bacterial lawn.

In a second aspect, the present invention provides polypeptide having an amino acid sequence selected from the group consisting of: SEQ ID NO:8-54

In a third aspect, the present invention provides a $V_H$ antibody fragment comprising at least one amino acid sequence selected from the group consisting of: SEQ ID NO:8-22.

In a fourth aspect, the present invention provides a $V_L$ antibody fragment comprising at least one amino acid sequence selected from the group consisting of: SEQ ID NO:23-54.

In a fifth aspect, the present invention provides A method for producing polypeptides with desirable biophysical properties, comprising the steps of a) providing at least one first nucleic acid sequence that encodes an antibody fragment or that encodes a polypeptide sequence, and having a first desirable property; b) providing at least one second nucleic acid sequence that encodes an antibody fragment having a second desirable property; c) cutting the at least one first and at least one second nucleic acid sequences into random fragments; d) reassembling the random fragments; e) expressing the random fragments; and f) screening the expressed random fragments for the first and second desirable properties.

DETAILED DESCRIPTION OF THE DRAWINGS

Figure Legends

FIG. 1. A pictorial representation of selected example results: The contrast in plaque size between phages displaying a soluble $V_H$ (HVHP428) and those displaying an insoluble one (BT32/A6). The photo depicts a part of the bacterial lawn agar plate which was magnified to enhance plaque visualization. Although the plate contained an equal number of each of the two plaque types, the photo essentially contains the large, HVHP428 plaques. The majority of the BT32/A6 plaques were too small to produce clear, well-defined images in the photo. The plaques marked by arrows, thus, represent a minor proportion of BT32/A6 phages which were large enough to be visible in this image. Asterisks marks representative plaque sizes for HVHP428 phages. The identities of plaques were determined by DNA sequencing.

Figure 2:
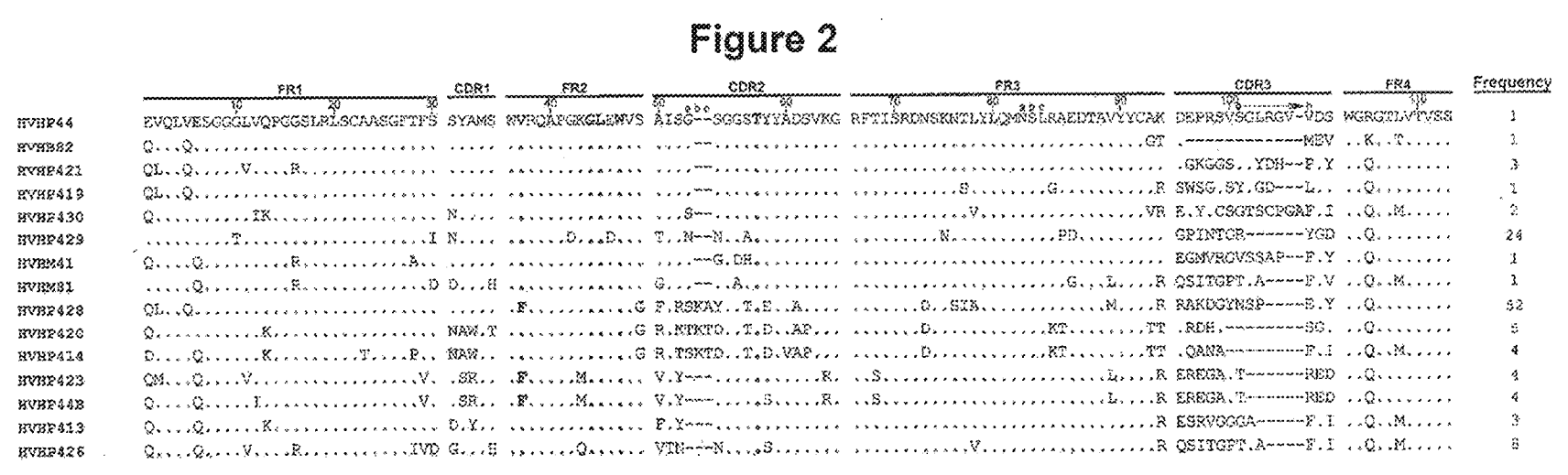

FIG. 2. Amino acid sequence of the human $V_H$s selected based on affinity for protein A and plaque size (SEQ ID NOS.: 8-22 disclosed respectively in order of appearance). The dots in the sequence entries indicate amino acid identity with HVHP2M10 or HVHP44. Dashes are included for sequence alignment. Residues at the key solubility positions and residue 57T which associates with $V_H$s/$V_H$Hs with protein A binding property are in bold. The Kabat numbering system is used. The total "frequency" value is 114. CDR=complementarity determining region; FR=framework region; gln seq=germline sequence FIGS. 3A, 3B, 3C and 3D. Aggregation tendencies of the human $V_H$s. 3A Gel filtration chromatograms comparing the oligomerization state of a human $V_H$ isolated in this study (HVHP428) to that of a llama $V_H$H (H11C7) and a typical human $V_H$ (BT32/A6). The peak eluting last in each chromatogram corresponds to monomeric $V_H$. The dimeric H11C7 peak is marked by an arrow. 3B, C and D One-dimensional $^1$H NMR spectra of HVHP414 at 800 MHz (3B), HVHP423 at 500 MHz (3C) and HVHP428 at 800 MHz (3D). The spectra in the left panel are scaled up by a factor of two to enable better viewing of low-intensity signals.

Figure 4B:
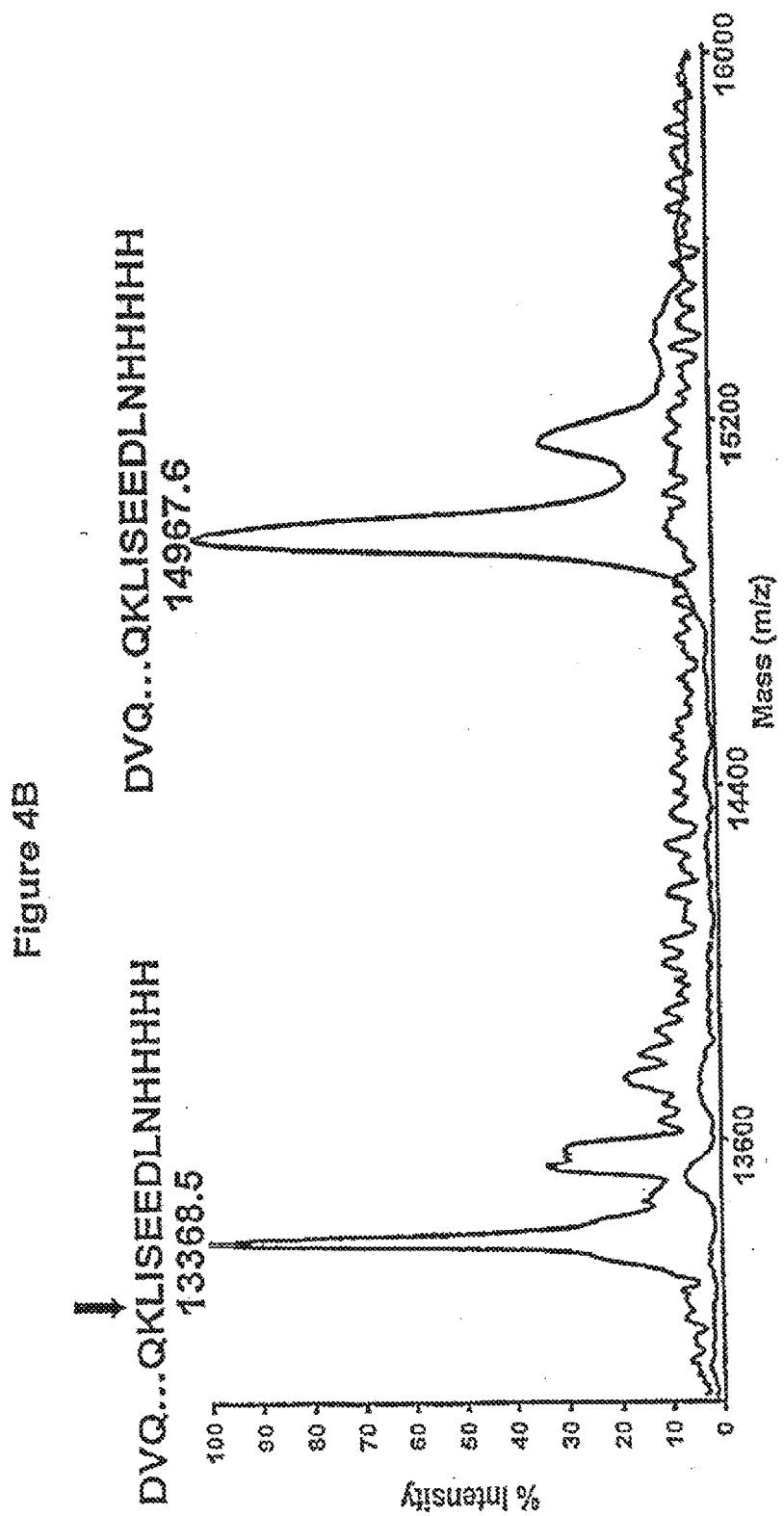

FIGS. 4A, 4B and 4C. Stability of the human $V_H$s in terms of their resistance to trypsin at 37° C. and integrity following long incubation at 37° C. 4A, SDS-PAGE comparing the mobilities of the untreated and trypsin-treated HVHP414 $V_H$ at 15, 30 and 60 min relative to a 21 kDa marker. HVHP414-cMyc denotes HVHP414 $V_H$ lacking the c-Myc. 4B, Molecular mass profiles obtained by mass spectrometry of untreated and trypsin-treated (60 min) HVHP414 $V_H$ (SEQ ID NO.: 18). The mass spectrometry profile of the treated $V_H$ is superimposed onto that for the untreated one to provide a better visual comparison. The experimental molecular mass of the untreated $V_H$ is 14,967.6 Da, which is essentially identical to the expected molecular mass, 14,967.7 Da. The observed molecular mass of the trypsin-treated $V_H$ (13,368.5 Da) indicates loss of 13 amino acids at the C-terminus by cleavage at K (Lys) in the c-Myc tag to give an expected molecular mass of 13,368.0 Da. The trypsin cleavage site is shown by a vertical arrow above the amino acids sequence of HVHP414. 4C, Gel filtration chromatograms comparing the oligomerization state of the 37° C.-treated HVHP420 $V_H$ (upper profile) to that of untreated $V_H$ (lower profile). The chromatograms were shifted vertically because they were indistinguishable when superimposed. The major and minor peaks in each chromatogram correspond to monomeric and dimeric $V_H$s, respectively. The dimeric $V_H$ constitutes 3% of the total protein. The inset shows the sensorgram overlays for the binding of 37° C.-treated HVHP420 to protein A at various concentrations. The $V_H$s used for temperature stability studies were from stocks which had already been at 4° C. for several months.

Figure 5:
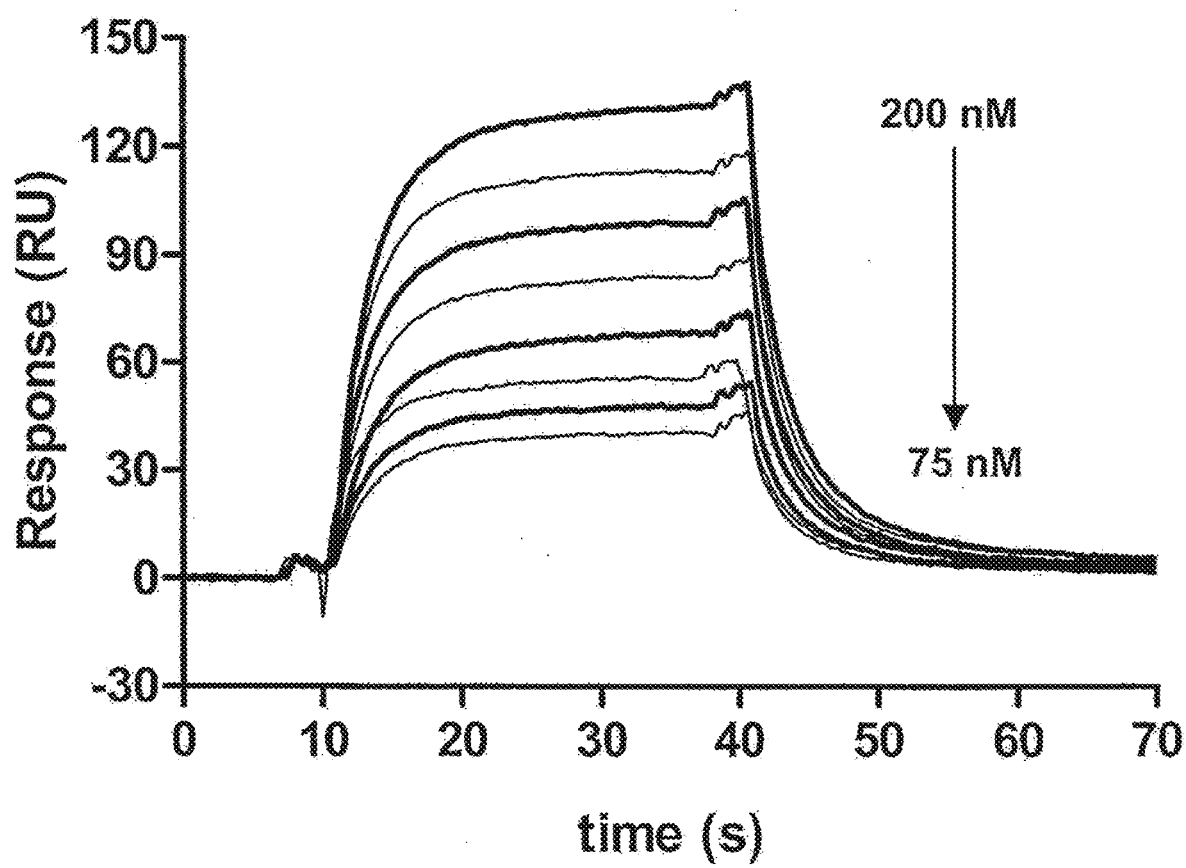

FIG. 5. Sensorgram overlays showing the binding of native (thick lines) and refolded (thin lines) HVHP423 to immobilized protein A at 75, 100, 150 and 200 nM concentrations. $K_D$n and $K_D$ ref were calculated from respective sensorgrams and used to determine RE as described below.

Figure 6:
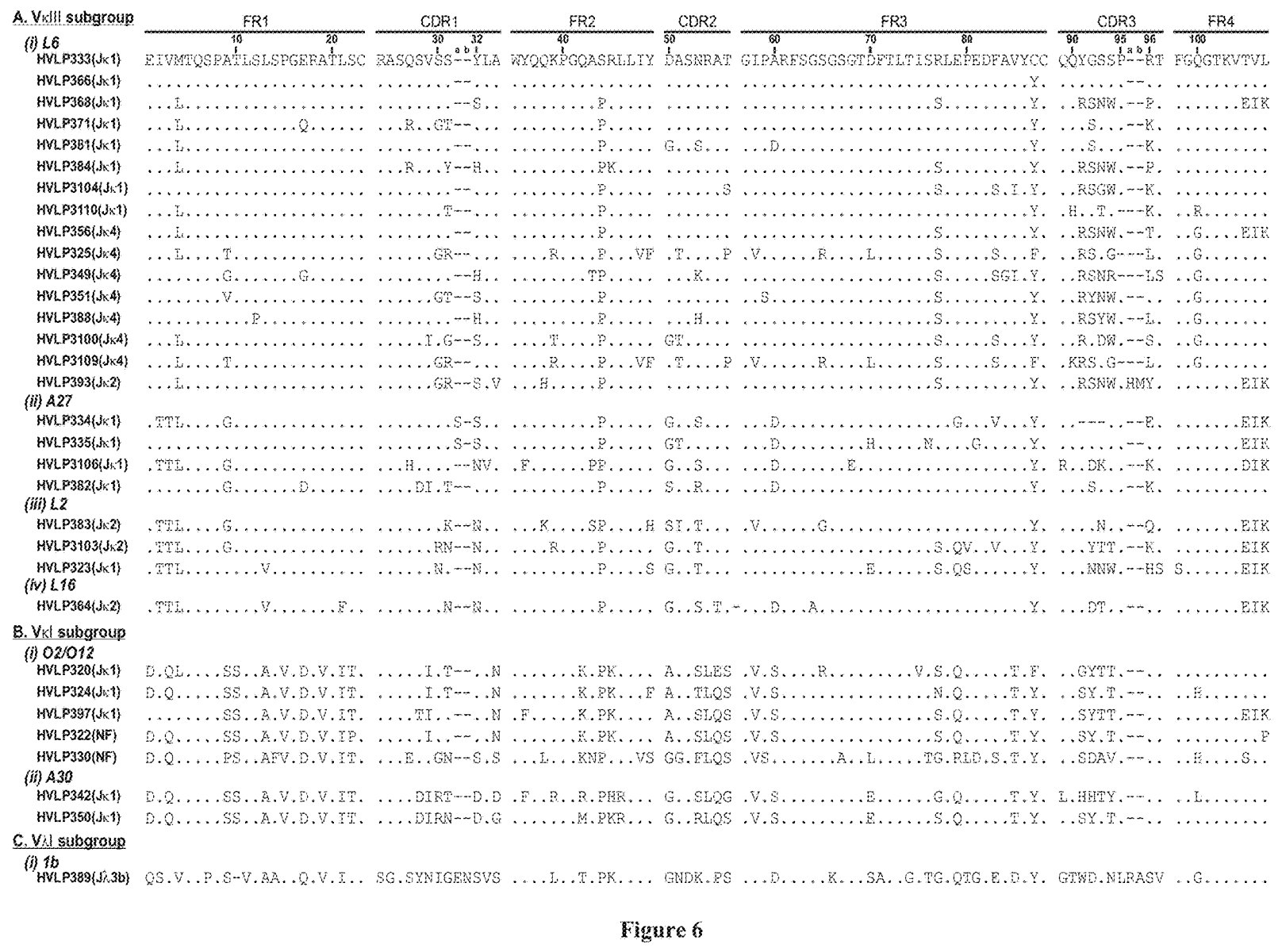

FIG. 6. Amino acid sequences of the human Vis selected based on affinity for protein L and plaque size (SEQ ID NOS.: 23-54 disclosed respectively in order of appearance). The dots in the sequence entries indicate amino acid identity with HVLP333. Dashes are included for sequence alignment. See the V BASE for sequence numbering and CDR designation. L6, A27, L2, L16, O2/O12, A30 and 1b are V germline designation. J germline designations are in the brackets. NF, not found.

Figure 7A:
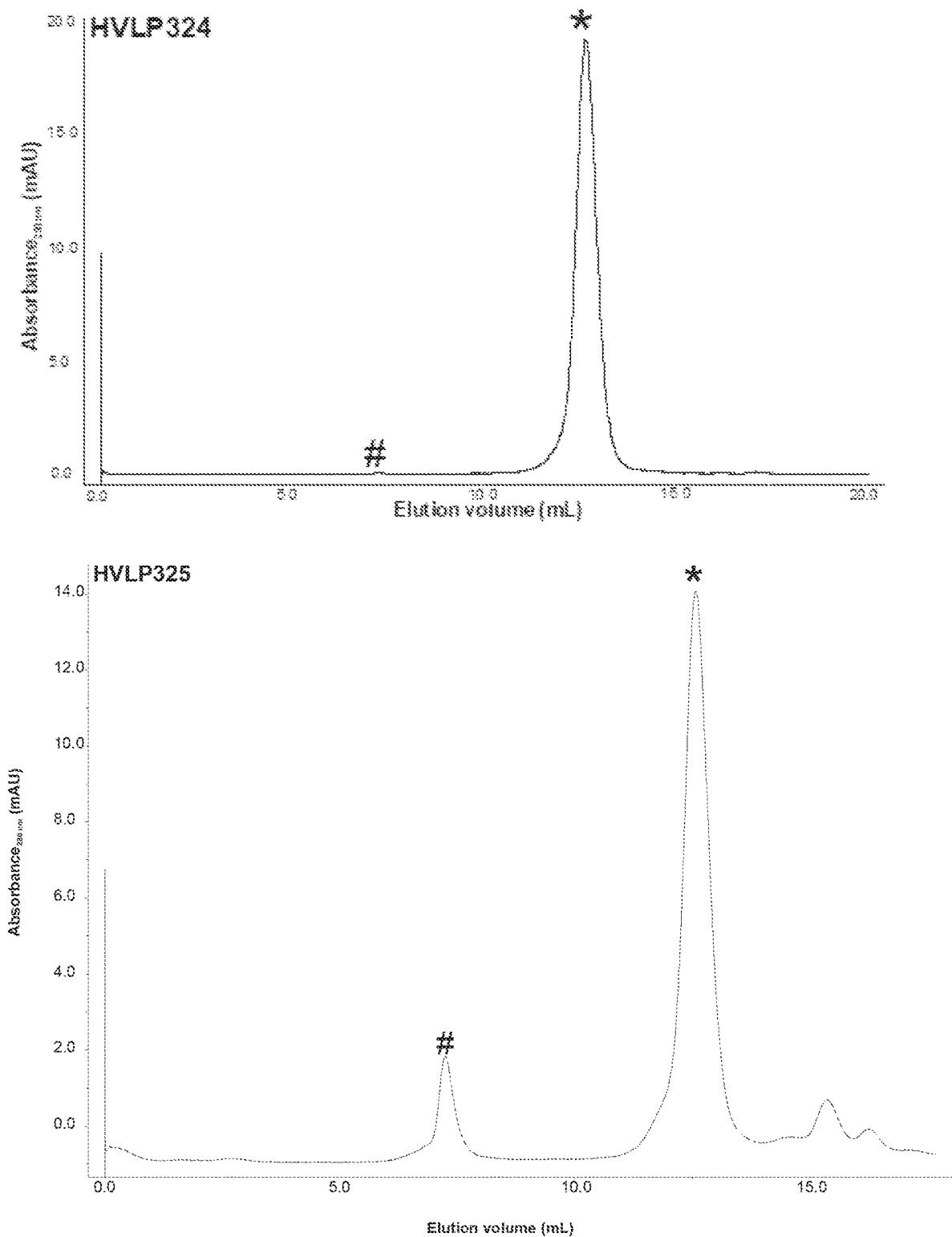
Figure 7B:
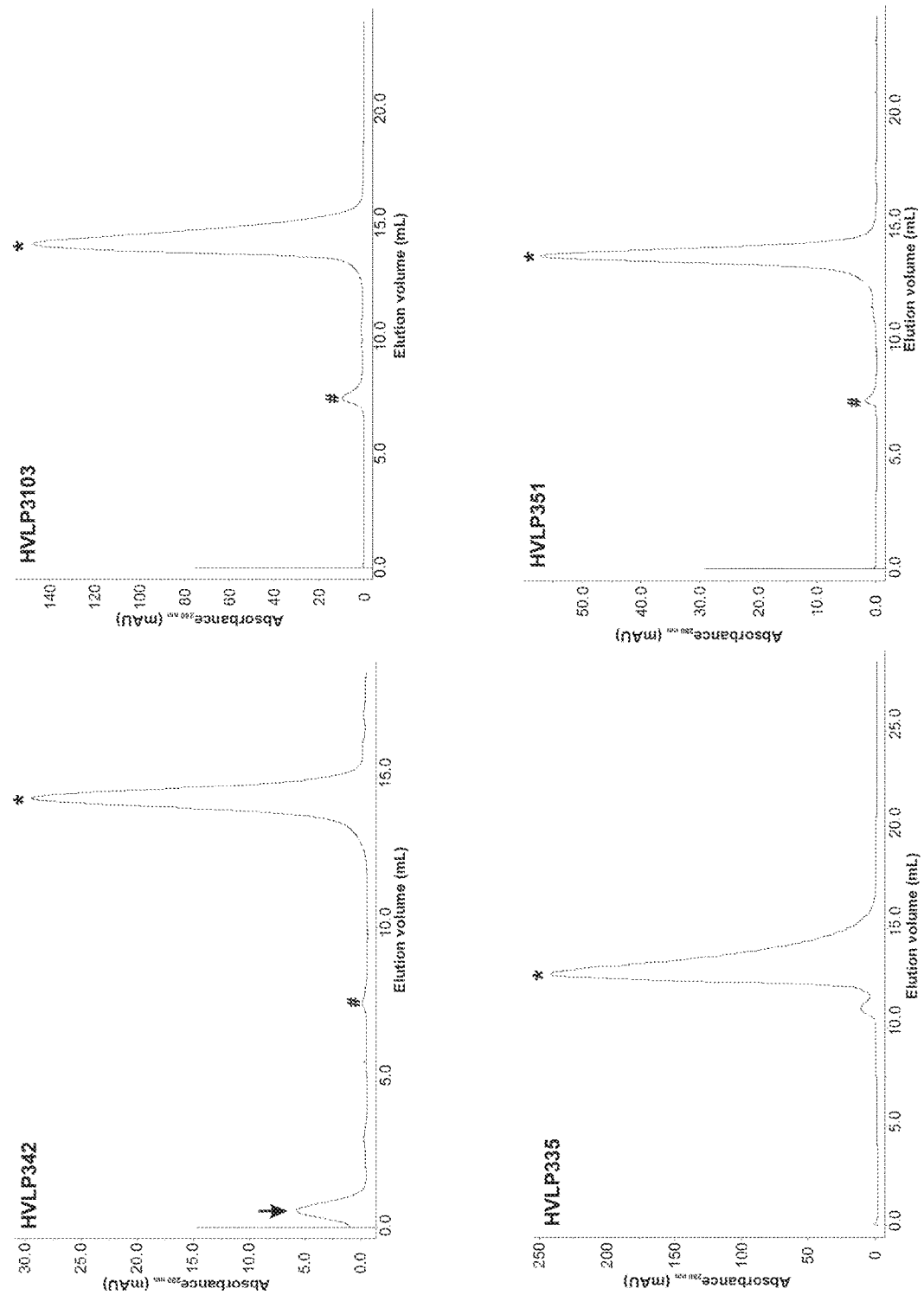

FIGS. 7A, 7B. Size exclusion chromatograms of human $V_L$ domains. In 7A, the $V_L$s were applied at a concentration of 0.6 mg/ml. In 7B, the $V_L$s were applied at their highest concentration available: HVLP342, 1.0 mg/ml; HVLP3103, 5.9 mg/ml; HVLP335, 4.9 mg/ml; HVLP351, 0.89 mg/ml. "#" and "*" represent aggregate and monomer peaks, respectively. The aggregates elute in the exclusion volume. The peak marked by an arrow in the HVLP342 panel (B) is the carry over from a previous run.

Figure 8:
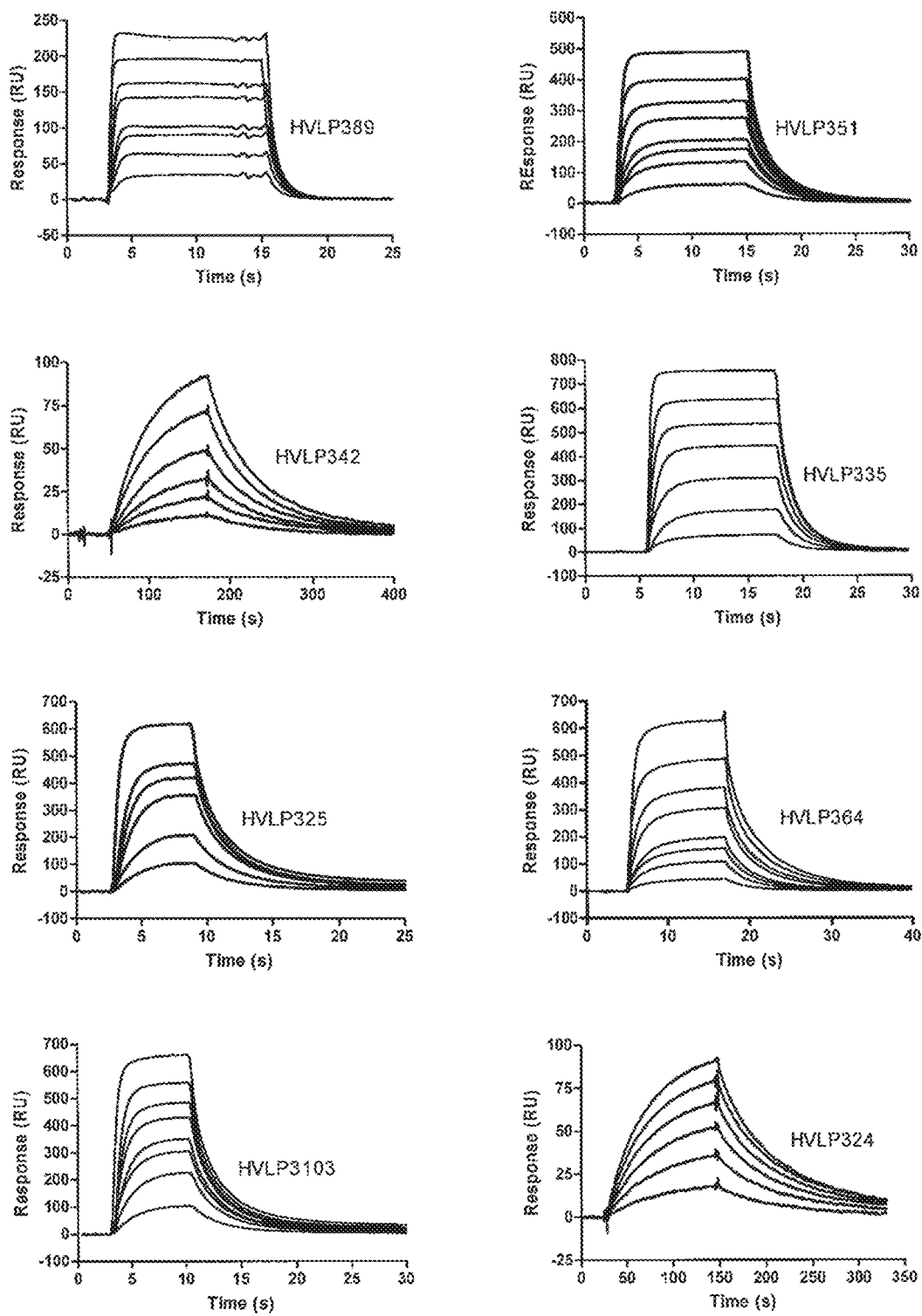

FIG. 8. Sensorgram overlays showing the binding of $V_L$s to immobilized protein L at concentrations of 0.2, 0.5, 0.75, 1, 2, 3, 5 and 10 µM (HVLP389, HVLP351 and HVLP364); 1, 2, 3, 5, 7.5 and 10 nM (HVLP342); 0.2, 0.5, 1, 2, 3, 5 and 10 µM (HVLP335); 0.2, 0.5, 1, 1.5, 2 and 5 µM (HVLP325), 0.2, 0.5, 0.75, 1, 1.5, 2 and 5 µM (HVLP3103) and 1, 2, 3, 4, 5 and 6 nM (HVLP324). The sensorgrams for HVLP324 and HVLP342 bindings to the low affinity site of protein L are not included but the calculated $K_D$s are recorded in Table 3.

Figure 9A:
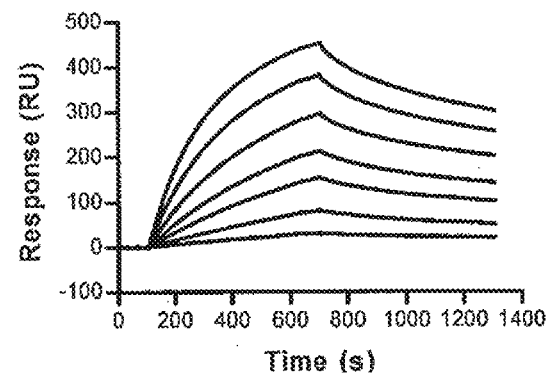
Figure 9B:
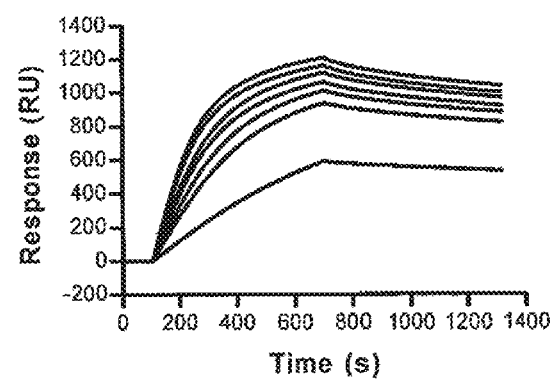

FIGS. 9A, 9B. Bindings of HVHP328PTV2 to protein A and HVLP335PTV2 to protein L in surface plasmon resonance experiments. (9A) Sensorgram overlays showing the binding of HVH28PTV2 to immobilized protein A at 1, 2, 3, 4, 6, 8 and 10 nM concentrations. (9B) Sensorgram overlays showing the binding of HVLP335PTV2 to immobilized protein L at 1, 2, 2.5, 3, 3.5, 4 and 4.5 nM concentrations. The binding data are recorded in Table 4.

Figure 10:
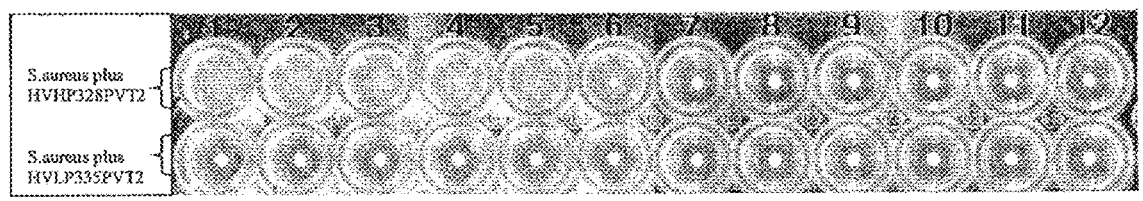

FIG. 10. Figure showing the results of the microagglutination experiments with *S. aureus* cells. The concentration of the pentamers decreases two-fold from well 1 to well 11 with well 12 having the pentamers replaced with PBS buffer. The top row wells contain HVHP328PTV2 pentamer and the bottom ones HVLP335PTV2 pentamer. The concentrations of the pentamers in wells 1 to 6 are 215, 108, 54, 27, 13 and 7 µg/ml, respectively.

DETAILED DESCRIPTION OF THE INVENTION

It is desirable to identify polypeptides, especially antibody fragments, that are of human origin, soluble, stable, resistant to aggregation, refoldable, highly expressed, easily manipulated at the DNA level, ideal for library construction and for 3-D structural determinations. Such antibody fragments are useful for a wide variety of immunotherapeutical applications, and also as diagnostic and detection agents. Human monomeric $V_H$ and $V_L$ antibodies are of particular interest, as they are likely to have many of the above-mentioned properties.

Polypeptides with the above-mentioned properties may be identified by high throughput screening of libraries capable of expressing a variety of polypeptide sequences. For example, phage display libraries (preferably filamentous phage such as M13 or fd) may be screened by infecting a field of bacteria susceptible to the phage (a bacterial lawn) with the phage, then determining which phages have successfully lysed the bacteria by looking for clear, bacteria-free areas known as plaques. Phages displaying monomeric llaminated $V_H$s and $V_L$s form larger plaques on bacterial lawns than phages displaying fully human $V_H$s with aggregation tendencies. Thus, plaque size may be used as a means of identifying rare, naturally-occurring monomer $V_H$s and $V_L$s from the human $V_H$ repertoire.

The method disclosed herein is also useful in identifying soluble, stable (stability covers a number of characteristics, including but not limited to high thermal refolding efficiency, high melting temperature, maintaining functionality after long (several days) incubation at 37° C., resistant to chemical denaturants, resistant to proteases, having a long shelf life at below 0° C., and 4° C., and at room temperature, maintaining functionality in intracellular environments, and maintaining functionality inside the human body, such as in the bloodstream) and high expressing proteins of differing origins, including:
1. $V_H$s, $V_L$S, Fabs, scFvs and whole antibodies such as IgGs, more specifically human ones
2. Protein variants based on non-antibody scaffolds single-chain T-cell receptors, T-cell receptor domains, transferin, lipocalins, kunitz domains, ankyrin repeats, and cytotoxic T-lymphocyte-associated antigen (CTLA-4), including human ones
3. Vaccines such as viral and bacterial protein vaccines
4. Therapeutic proteins, e.g., insulin, growth hormone, arythropoietin
5. Proteinacious diagnostic and biochemical reagents, e.g., protein A, protein G.

Once polypeptides have been identified by this method, they can be used to construct additional libraries. This is done by selecting a nucleic acid sequence of, for example, a VH. Oligonucleotides with randomized codons are created and incorporated into the VH sequence. Thus, each unique oligonucleotide is incorporated into a VH gene, and the modified VH genes constitute a library of sequences with slight variations. Typically, the oligonucleotides are designed such that the CDRs or loops of the VH are randomized. For example, one, two or all three of VH CDRs may be randomized. The VH library is then cloned into an appropriate vector, depending on the type of library to be used, and the nucleic acid sequences are expressed as polypeptides. The library is screened for molecules that bind to the library polypeptides, typically by panning. The libraries may be phage display libraries, or other display libraries such as ribosome display and yeast display.

Polypeptides identified by the method discussed herein may be used for immunotherapy by, for example, the cross-linking of monomers to form dimers, trimers, pentamers and other multimers. This may result in better affinity for antigen molecules and slower dissociation rates for some antigens. Another possible approach is to link or fuse polypeptides to a variety of molecules with various functions. For example, antibody fragments may be linked to radionuclides, cytotoxic drugs, toxins, peptides, proteins, enzymes, liposomes, lipids, T-cell superantigens or viruses in order to target and destroy or modify specific cells or molecules.

Once the $V_H$s or $V_L$s identified by the selection method described herein have been isolated, they can be further manipulated to select for improved biophysical properties such as solubility, stability, monomericity, binding specificity, human origin or high expressability. This can be achieved by in vitro recombination techniques such as DNA shuffling or a staggered extension process. DNA shuffling involves cutting the nucleic acid sequence of first (donor) and second (acceptor) polypeptides, such as antibody fragments, into random fragments, then reassembling the random fragments by a PCR-like reaction. The reassembled fragments are then screened to select for the desired properties.

For example, one or more VHs with high stability (donors) can be mixed with one or more VHs lacking sufficient stability (acceptors) and subjected to DNA shuffling. This generates mutants of the acceptor VHs which have incorporated stability residues from the donor VHs. The newly stable mutants can be identified by the methods described herein, or through other evolutionary protein screening systems such as ribosome display, yeast display, bacterial cell display and phage display. Similarly, this technique can be used to transfer desirable traits such as solubility, monomericity, and high expression.

This technique may be used where both donor and acceptor $V_H$s have desirable properties, to produce a $V_H$ with both properties. For example, an unstable donor $V_H$ which binds to an important therapeutic or diagnostic ligand can be shuffled with a stable acceptor $V_H$. In order to ensure that new generated stable $V_H$s also have the ability to bind to the ligand, the screening system may involve a ligand binding step.

DNA shuffling may also be useful for humanizing non-human $V_H$s such as camelid heavy chain antibody variable domains and nurse shark and wobbegong shark variable domains, or non-human $V_L$s which bind to therapeutic targets. Human $V_H$s and $V_L$s with desirable properties such as solubility, stability, monomericity and high expressability may be used as donors. For example, one or more human $V_H$s with good stability (donors) can be mixed with one or more non-human therapeutic $V_H$s (acceptors) and subjected to DNA shuffling. This generates mutants of the acceptor $V_H$s which are both stable and humanized. The newly generated humanized and stable mutants can be identified by the methods described herein, or through other evolutionary protein screening systems such as ribosome display, yeast display, bacterial cell display and phage display. In a further example, the acceptor $V_H$ could be a therapeutic $V_H$H (camelid heavy chain antibody variable domain).

Further, this technique is also useful for selecting desirable properties of polypeptides other than $V_H$s and $V_L$s. As discussed above, the donor polypeptide and the acceptor polypeptide may be both human, or the donor may be human and the acceptor non-human.

A possible approach for imparting solubility, monomericity, high expressability or stability to $V_H$s and $V_L$s may be through grafting complementarity determining regions (CDRs) onto acceptor $V_H$s and $V_L$s. Since CDRs are known to be involved in the solubility and stability of single-domain antibodies, and accordingly the grafting of these regions, such as the CDRs from $V_H$s and $V_L$s isolated by the methods described herein, may impart solubility and/or stability to acceptor $V_H$s and $V_L$s.

Human Monomeric $V_H$s and $V_L$s

Several monomeric human $V_H$s with different germline and overall sequences were identified (see FIG. 2 and SEQ ID NO. 8 through 22) from a naïve human $V_H$ phage display library by this selection method based on phage plaque size. The $V_H$s remain functional and monomeric following trypsin treatment at 37° C., weeks of incubations at 37° C. or months of storage at 4° C., have high thermal refolding efficiencies, are produced in good yields in *E. coli* and possess protein A binding activity.

In addition, several monomeric human $V_L$s were identified (see FIG. 6 and SEQ ID NO. 23 through 54). The $V_L$s are also produced in good yields in *E. coli* and possess protein L binding activity.

Such properties will also be manifested by $V_H$s from synthetic libraries that utilize the above $V_H$s as scaffolds. Thus, such libraries may yield therapeutic or diagnostic $V_H$s which would have good efficacy at physiological temperature, extended shelf life and a cost-effective production. High thermal refolding efficiency characteristic would further extend the biotechnological applications of these libraries to situations where $V_H$ binders are required to maintain their activity after exposure to transient high temperatures. The $V_H$s should also be very suitable for intrabody applications because of their desirable biophysical properties. The protein A binding property will simplify $V_H$ purification and detection in diagnostic tests, immunoblotting and immunocytochemistry and can be exploited to enhance library performance by removing nonfunctional $V_H$s from the libraries. Similarly, libraries that utilize $V_L$s as scaffolds will yield therapeutic or diagnostic VAS which have similarly desirable properties. Since $V_L$s bind with protein L, $V_L$ purification and detection is simplified by taking advantage of this protein L binding property.

Display libraries built on the present $V_H$s and $V_L$s may also be a useful source of diagnostics and detection agents.

Previously reported fully human $V_H$s with favorable biophysical properties were based on a single V germline sequence: DP-47 ((Jespers, L. et al., 2004b; Jespers, L. et al., 2004a). The observation that the monomeric human $V_H$s in this study stem from six different germline sequences including DP-47, demonstrates that stable $V_H$s are not restricted in terms of germline gene usage. In fact, it is very likely that we would have isolated monomeric $V_H$s of family and germline origins different from the ones we describe here had we not restricted our selection to a subset of $V_H$3 family $V_H$s with protein A binding activity. It is not possible to pinpoint amino acid mutations (Table 1) responsible for the observed biophysical behavior of the present $V_H$s due to the occurrence of multiple mutations in $V_H$s and the fact that CDR3 is also known to be involved in shaping the biophysical profiles of sdAbs. It may be, however, that mutations at positions known to be important for sdAbs stability and solubility, eg., V37F in HVHP423 and HVHP44B, or mutations occurring multiple times at the same position, e.g., L5V/Q and V5Q in nine $V_H$s, have a role in determining $V_H$s biophysical properties. In terms of library construction, it would be desirable that the monomericity of the present $V_H$s not be dependent on CDRs, in particular CDR3, so that CDR randomization be performed without the worry of jeopardizing library stability. In this regard, the $V_H$s with smaller CDR3, e.g, HVHB82, may be preferred scaffolds since there would be less dependence on CDR3 for stability.

The diversity of the present $V_H$s and $V_L$s in terms of overall sequence and CDR3 length should allow the construction of better-performing libraries. Synthetic $V_H$ libraries have been constructed on single scaffolds. Such an approach to repertoire generation is in sharp contrast to the natural, in vivo "approach" which utilizes a multiplicity of scaffolds. Based on the sequences reported here one can take advantage of the availability of the diverse set of $V_H$s and $V_L$s and create libraries which are based on multiple $V_H$ and $V_L$ scaffolds. Such libraries would be a better emulation of in vivo repertoires and therefore, would have a more optimal complexity. Of the three CDRs in sdAbs, CDR3 generally contributes most significantly to repertoire diversity and for this reason CDR3 randomization on $V_H$ and $V_L$ scaffolds are typically accompanied by concomitant varying of CDR3 length. While this significantly improves library complexity, it may also compromise library stability by disrupting the length of the parental scaffold CDR3. The heterogeneity of the $V_H$s and $V_L$s disclosed herein in terms of CDR3 length permit the creation of libraries with both good complexity, good stability and good biophysical characteristics. Such libraries would preferably consist of sub-libraries, where each sub-library is created by CDR3 randomization (and CDR1 and/or CDR2 randomization, if desired) on a single $V_H$ or $V_L$ scaffold without disrupting the parental CDR3 length.

The versatility of the present $V_H$s and $V_L$s is also beneficial in terms of choosing an optimal $V_H$ or $V_L$ framework for humanizing $V_H$Hs, $V_H$s and $V_L$s which are specific to therapeutic targets. High affinity camelid $V_H$Hs against therapeutic targets can be obtained from immune, non-immunized or synthetic $V_H$H libraries with relative ease and be subsequently subjected to humanization (CDR grafting, resurfacing, deimmunization) to remove possible $V_H$H immunogenicity, hence providing an alternative to human $V_H$ library approach for production of therapeutic $V_H$s.

Generating high affinity therapeutic $V_H$s by the latter approach may often require additional tedious and time consuming in vitro affinity maturation of the lead binder(s) selected from the primary synthetic human $V_H$ libraries.

Nonhuman $V_H$s against therapeutic targets can be obtained from immune, non-immunized or synthetic $V_H$ libraries with relative ease and be subsequently subjected to humanization (CDR grafting, resurfacing, deimmunization) to eliminate nonhuman $V_H$ immunogenicity, hence providing an alternative to human $V_H$ library approach for production of therapeutic $V_H$s.

Nonhuman Vis against therapeutic targets can be obtained from immune, non-immunized or synthetic $V_H$H libraries with relative ease and be subsequently subjected to humanization (CDR grafting, resurfacing, deimmunization) to eliminate $V_H$H immunogenicity, hence providing an alternative to human $V_L$ library approach for production of therapeutic $V_L$s.

A number of evolutionary approaches for selection of proteins with improved biophysical properties have been described (Forrer, P. et al., 1999; Waldo, G. S., 2003); (Jespers, L. et al., 2004a; Jung, S. et al., 1999; Matsuura, T. et al., 2003). Typically, stability pressure is required to ensure preferential selection of stable variants over unstable or less stable ones from a library population. For example, in a related work, heat treatment of $V_H$ phage display libraries was required to select aggregation resistant $V_H$s (Jespers, L. et al., 2004a). Examples of evolutionary selection approaches involving phage display include conventional phage display, selectively infective phage and the proteolysis approaches. In the first two approaches affinity selection is used to select stable species from a library, based on the assumption that stable proteins possess better binding properties for their ligand than the unstable ones. However, even with the additional inclusion of a stability selection step, these approaches may primarily enrich for higher affinity rather than for higher stability (Jung, S. et al., 1999). A binding step requirement also limits the applicability of these approaches to proteins with known ligands. The third, proteolysis approach is based on the fact that stable proteins are generally compact and therefore are resistant to proteases whereas the unstable ones are not. The phage display format is engineered in such a way that the protease stability of the displayed protein translates to phage infectivity. Thus, when a variant phage display library is treated with a protease, only the phages displaying stable proteins retain their infectivity and can subsequently be selected by infecting an E. coli host. Since this approach is independent of ligand binding, it has general utility. However, even stable and well folded proteins have protease sensitive sites, e.g., loops and linkers, and this could sometimes hinder the selection of stable species in a proteolysis approach (Bai, Y. et al., 2004).

By contrast, in the present evolutionary approach, proteins with superior biophysical properties are simply identified by the naked eye. The approach does not require ligand binding, proteolysis or destabilization steps, and thus, avoids complications which may be encountered in the reported selection approaches. No requirement for a binding step also means that this approach has general utility. As an option, a binding step may be included to ensure that the selected proteins are functional. However, the dependency of the present approach on plating (for plaque visualization) introduces a possible logistical limitation in terms of the number of plates that can be handled and thus limits its application to smaller libraries.

Nonetheless, the utility of the current approach can be extended to large libraries, if the library is first reduced to a manageable size. This can be done, for example, by incorporating into the selection system a step which would remove large populations of unstable species, e.g., library adsorption on a protein A surface, or on a hydrophobic interaction column to remove poorly folded proteins with exposed hydrophobic surfaces (Matsuura, T. et al., 2003). Here, the approach was used to select $V_H$s and $V_L$s of good biophysical properties in a background of very unstable $V_H$s and $V_L$s. However, it may be more difficult to select the "best" species from a mutant library which is populated with proteins with reasonably good stabilities. In this case, the lead variants may be identified based on the rate of plaque formation by using shorter incubation times, or based on plaque size and frequency criteria.

The present selection approach can be extended to identification of stable and well-folded antibody fragments such as scFvs and Fabs with the optional inclusion, in the selection system, of a binding step involving protein L, A or any ligand, as well as stable non-antibody scaffolds and variants thereof. Moreover, the observed correlation between phage plaque size and $V_H$ expression yield means that one can utilize the present approach for acquiring high-expressing versions of proteins with otherwise poor or unsatisfactory expression from mutant phage display libraries. This application would be particularly appealing in the case of therapeutic proteins or expensive poor-expressing protein reagents where boosting protein expression would significantly offset protein production cost.

Binding Analyses of Pentamers

Both $V_L$s and $V_H$s are amenable to pentamerization and the pentamerization can be used to quickly convert a low affinity $V_L$ or $V_H$ monomer to a high affinity $V_L$ or $V_H$ pentamer. Such pentamers are invaluable diagnostics and detection agents. In such applications, the binding of a $V_L$ or $V_H$ pentamer to its target can be detected by a reporter molecule such as an enzyme (for example, horse radish peroxidase or alkaline phosphatase), or a fluorescent molecule conjugated to the pentamer. Alternatively, the binding of the pentamer can be detected by a secondary molecule which is conjugated to a reporter molecule. The secondary molecule can be specific to the pentamer itself or to a tag thereof, such as a 6His tag (SEQ ID NO.: 55) or c-Myc tag. For example, a typical secondary molecule is an immunoglobulin.

The interactions between the $V_H$s and protein A and Vis with protein L are fundamentally different from those between $V_H$s and $V_L$s with their target antigens. The antigen binding of a $V_H$ or a $V_L$ involves three antigen binding loops which form the combining site of an antibody domain. The protein A binding of a $V_H$ with protein A binding activity and a $V_L$ with protein L binding activity involve binding sites and residues on the antibody domains that are totally distinct from the antibody combining site. Thus, a $V_H$ with protein A binding activity can simultaneously bind to protein A and its target antigen and a $V_L$ with protein L binding activity can simultaneously bind to protein L and its target antigen. Since the present $V_H$s and $V_L$s have affinity for protein A and L, respectively, protein A and L can be used as the secondary molecule for detection and diagnostic applications mentioned above. The human $V_H$ and $V_L$ pentamers can also be used for therapy.

Pathogen Detection by the Pentamers

The protein A and L binding activity of the $V_H$s and $V_L$s can be used to detect bacteria which have protein A and/or L on their surfaces. Protein A is present on the surface of the pathogenic bacteria, Staphylococcus aureus. Thus, the $V_H$s with protein A binding activity such as the ones described here can be used to detect S. aureus. Similarly, the $V_L$ monomers and $V_L$ pentamers with protein L binding activity can be used for the detection of bacteria, in particular pathogenic bacteria such as Peptostreptococcus magnus, which have protein L on their cell surface.

Protein L is implicated as a virulent factor in the pathogenesis of P. magnus (Ricci, S. et al., 2001) in humans. In vaginosis, protein L is thought to exert its effect by cross-linking surface associated IgE. $V_L$ monomers and/or pentamers with protein L binding activity have potential as therapeutics since they could interfere with the IgE cross-linking action of protein L.

Protein A is implicated as a virulent factor in the pathogenesis of S. aureus in humans (Fournier, B. et al., 2004). Its virulence has been attributed to its ability to interact with host components including binding to antibodies. $V_H$ monomers and/or pentamers with protein A binding activity have potential as therapeutics since they could interfere with the interaction of of protein A with host components.

EXAMPLES

Identification and Sequence Analysis of Monomeric Human $V_H$s

During the course of the construction of fully human and llaminated human $V_H$ libraries, it was learned that the phages displaying monomeric llaminated $V_H$s formed larger plaques on bacterial lawns than phages displaying fully human $V_H$s with aggregation tendencies. Thus, plaque size was used as a means of identifying rare, naturally-occurring monomer $V_H$s from the human $V_H$ repertoire (FIG. 1). To this end, a phage library displaying human $V_H$s with a size of 6×10$^8$ was constructed and propagated as plaques on agar plates. On the titer plates, the library consisted essentially of small plaques interspersed with some large ones. PCR on twenty clones revealed that the small plaques corresponded to the $V_H$-displaying phages while the large ones represented the wild type phages, i.e., phages lacking $V_H$ sequence inserts. None of the $V_H$-displaying phages were found with large plaque morphology. This was not unexpected due to the paucity of the monomeric $V_H$s in the human repertoire and the large size of the library. To facilitate the identification of monomeric $V_H$s, it was decided to reduce the library to a manageable size and remove the interfering wild type phages with large-plaque-size morphology by panning the library against protein A which binds to a subset of human $V_H$s from $V_H$3 family.

Following a few rounds of panning, the library became enriched for phage producing large plaques, and PCR and sequencing of more than 110 such plaques showed that all had complete $V_H$ open reading frames. The size of the large plaques which were picked for analysis is represented in FIG. 1. Sequencing revealed fifteen different $V_H$s which belonged to the $V_H$3 family and utilized DP-38, DP-47, V3-49, V3-53, YAC-5 or 8-1B germline V segments (Table 1; FIG. 2). DP-38 and DP-47 germline sequences have been previously implicated in protein A binding. In addition, all $V_H$s had a Thr residue at position 57 (FIG. 2), consistent with their protein A binding activity. The most frequently-utilized germline V segment was DP-47 which occurred in over 50% of the $V_H$s, but the most frequent clone (i.e., HVHP428; relative frequency 46%) utilized the V3-49 germline V segment. HVHP429 with a DP-47 germline sequence was the second most abundant $V_H$ with a relative frequency of 21% (FIG. 2). The $V_H$ CDR3 lengths ranged from 4 amino acids for HVHB82 to 16 amino acids for HVHP430 amino acids, with HVHP430 having a pair of Cys residues in CDR3. Amino acid mutations with respect to the parental germline V segment (residues 1-94) and FR4 (residues 103-113) sequences, were observed in all $V_H$s and ranged from two mutations for HVHP44 (L5V and Q105R) and HVHB82 (E1Q and L5Q) to sixteen mutations for HVHP426 (Table 1). Mutations were concentrated in the V segments; only two mutations were detected in all the fifteen FR4s, at positions 105 and 108. HVHP44 and HVHB82 differed from other $V_H$s in that they both had a positively-charged amino acid at position 105 instead of a Gln (Table 1; FIG. 2). However, while the positively-charged amino acid in HVHP44 was acquired by mutation, the one in HVHB82 was germline-encoded. Except for HVHP423 and HVHP44B, the remaining $V_H$s had the germline residues at the key solubility positions: 37V/44G/45L/47W or 37F/44G/45L/47W (HVHP428); HVHP423 and HVHP44B had a V37F mutation. Mutations at other positions which are shown or hypothesized to be important in $V_H$ solubility included seven E6Q, three S35T/H, one R83G and one K83R, one A84P and one T84A and one M108L. Frequent mutations were also observed at positions 1 and 5 which included eleven E1Q, eight L5V/Q and one V5Q mutations.

Biophysical Characterization of the Human $V_H$s

All $V_H$s except HVHP44B, which was essentially the same as HVHP423, were expressed in one-litre-culture volumes in E. coli strain TG1 in fusion with c-Myc-His5 tag and purified to homogeneity from periplasmic extracts by immobilized metal affinity chromatography (IMAC). The expression yields ranged from 1.8 to 62.1 mg of purified protein per liter of bacterial culture in shaker flasks with majority of $V_H$s having yields in several milligrams (Table 2). In the instance of HVHP423 and HVHP430, another trial under "apparently" the same expression conditions gave yields of 2.4 and 6.4 mg as opposed to 62.1 and 23.7 mg, respectively. This implies that for many of the $V_H$s described here optimal expression conditions should be achieved, without much effort, resulting in expression yields significantly higher than the reported values in Table 2. As expected, all the $V_H$s bound to protein A in surface plasmon resonance (SPR) analyses, with $K_D$s of 0.2-3 µM, a range and magnitude comparable to the ones reported previously for llama $V_H$H variants with protein A binding activity. None of the $V_H$s bound to the Fab reference surface.

The aggregation tendency of the human $V_H$s was assessed in terms of their oligomerization states by gel filtration chromatography and NMR (Table 2). All $V_H$s were subjected to SUPERDEX™ 75 gel filtration chromatography. Similar to a llama $V_H$H, i.e., H11C7, all $V_H$s gave a symmetric single peak at the elution volume expected for a monomer, and were substantially free of any aggregates (see the example for HVHP428 in FIG. 3A. In contrast, a typical human $V_H$ (i.e., BT32/A6) formed considerable amount of aggregates. For three of the $V_H$s, a minor peak with a mobility expected for a $V_H$ dimer was also observed. SPR analyses of the minor peaks gave off-rate values which were significantly slower than those for the monomer $V_H$s, consistent with them being dimers. The dimer peak was also observed in the case of the llama $V_H$H, H11C7. The folding and oligomerization states of the $V_H$s at high concentrations were further studied by NMR spectroscopy. As shown in Table II, all the $V_H$ proteins studied appeared to be relatively soluble and assumed a well-folded three-dimensional structure. One-dimensional NMR spectra of the $V_H$ fragments (FIG. 3B) showed structure folds characteristic of $V_H$ domains. The state of protein aggregation was also assessed by use of an PFG-NMR diffusion experiment for the HVHP414 fragment and two isoforms, VH14 and VH14-cMyc- with and without the c-Myc sequence, of the HVHP414. VH14 is a modified version of HVHP414 with a c-Myc N132E mutation and with an additional methionine residue at the N-terminus. In brief, the PFG-NMR data (not shown) indicated that all the protein samples had expected monomeric molecular weights even at the relatively high protein concentrations used for NMR experiments.

The stability of the $V_H$s was further investigated in terms of their resistance to trypsin at 37° C. integrity following long incubations at 37° C. Trypsin cleaves polypeptide amide backbones at the C-terminus of an Arg or a Lys residue. There are 9-13 Arg and Lys residues in the human $V_H$s (FIG. 2). There is also an additional Lys residue in the C-terminal c-Myc tag which is susceptible to digestion by trypsin. FIG. 4a is an SDS-PAGE analysis of HVHP414 during trypsin digestion. Within 1 h the original band was completely converted to a single product which had a mobility expected for the $V_H$ with no c-Myc-His5 tag. The same result was obtained for 12 other $V_H$s following a one-hour incubation with trypsin. Mass spectrometry on a randomly selected sample of the trypsin-treated $V_H$s (i.e., HVHP414, HVHP419, HVHP420, HVHP423, HVHP429, HVHP430 and HVHM81) confirmed that in every case the molecular mass of the digested product corresponded to a $V_H$ with the c-Myc Lys as the C-terminal residue. HVHM41 gave a significantly shorter fragment than the rest upon digestion, and in this case mass spectrometry experiments mapped the cleavage site to the Arg99 in CDR3 (data not shown).

Eleven $V_H$s ranging in concentration from 0.32 mg/ml (HVHP428) to 3.2 mg/ml (HVHP420) were incubated at 37° C. for 17 days. Their stability was subsequently determined in terms of oligomerization state and protein A binding. As shown by gel filtration chromatography, treatment of $V_H$s at 37° C. did not induce any aggregate formation: all $V_H$s gave chromatogram profiles which were virtually identical to those of untreated $V_H$s and stayed essentially as monomers (see the example for HVHP420; FIG. 4c). To ensure that the $V_H$s maintained their native fold following 37° C. treatment, two $V_H$s, namely, HVHP414 (1.2 mg/ml) and HVHP420 (3.2 mg/ml), were selected at random and their $K_D$s of binding to protein A were determined by SPR (Data shown for HVHP420; FIG. 4c inset) and compared to the $K_D$s obtained for untreated $V_H$s (Table 2). The calculated $K_D$s for the heat-treated $V_H$s were 1.4 µM and 1.0 µM for HVHP414 and HVHP420, respectively. These values are essentially identical to the corresponding values for the untreated $V_H$s (Table 2), demonstrating that 37° C. treatment of $V_H$s did not affect their native fold. The possibility that $V_H$s may have been in a less compact, non-native fold during the 37° C.-incubation periods and resumed their native fold upon returning to room temperature during gel filtration and SPR experiments is unlikely in light of the fact that the $V_H$s were resistant to trypsin at 37° C. (see above), a property typically associated for well folded native proteins.

The refolding efficiency (RE) of the human $V_H$s was investigated by comparing the $K_D$ s of the binding of the native ($K_D$n) and heat-treated, refolded ($K_D$ref) $V_H$s to protein A (Tanha, J. et al., 2002). When a fraction of the $V_H$ is inactivated by heat treatment the measured $K_D$ would be higher, since this parameter is based on the concentration of folded, i.e., active, antibody fragment. Thus, the ratio of $K_D$n to $K_D$ref gives a measure of $V_H$ RE. FIG. 5 compares sensorgrams for HVHP423 binding to immobilized protein A in native (thick lines) and refolded (thin lines) states at several selected $V_H$ concentrations. As can be seen, binding of the refolded $V_H$ to protein A is less in all instances, indicating that the unfolding is not fully reversible. For each of the 14 $V_H$s, protein A binding in both native and refolded states was measured at several concentrations, and the $K_D$s and subsequently REs were determined (Table 2; $K_D$ref values are not shown). The $K_D$s and REs of two anti-idiotypic llama $V_H$Hs, H11F9 and H11B2, which were used as references, were also determined. Four $V_H$s had REs in the range of 92%-95%, similar to the RE s for H11F9 and H11B2, 95% and 100%, respectively. Another five had RE s in the range of 84%-88% and three over 70%. Only two had significantly lower RE: HVHP413 (52%) and HVHP421 (14%). Several published $V_H$Hs examined previously had RE around 50% (van der Linden, R. H. et al., 1999).

Human $V_H$ phage display library construction and panning. cDNA was synthesized from human spleen mRNA (Ambion Inc., Austin, TX) using random hexanucletide primers and First Strand cDNA™ kit (GE Healthcare, Baie d'Urfé, QC, Canada). Using the cDNAs as template, $V_H$ genes with flanking CH sequences were amplified by polymerase chain reaction (PCR) in nine separate reactions using $V_H$ framework region 1 (FR1)-specific primers and an immunoglobin M-specific primer (de Haard, H. J. et al., 1999). The products were gel-purified and used as the template in the second round of PCR to construct $V_H$ genes using the FR1- and FR4-specific primers (de Haard, H. J. et al., 1999) that also introduced flanking ApaI I and Not I restriction sites for cloning purposes. The resultant $V_H$ repertoire DNAs were cloned into fd-tetGIIID phage vector and a $V_H$ phage display library was constructed (Tanha, J. et al., 2001). Panning against protein A (Amersham Biosciences Inc.) was performed as described (Tanha, J. et al., 2001). Germline sequence assignment of the selected $V_H$s was performed using DNAPLOT software Version 2.0.1 and V BASE version 1.0. Llama $V_H$Hs H11C7, H11F9 and H11B2 were isolated from a llama $V_H$H phage display library by panning against H11 scFv as described (Tanha, J. et al., 2002).

$V_H$ expression and purification. $V_H$s were cloned into pSJF2 expression vectors by standard cloning techniques (Sambrook, J. Fritsch E. F. and Maniatis T, 1989). Periplasmic expression of sdAbs and subsequent purification by immobilized metal affinity chromatography (IMAC) were performed as described (Muruganandam, A. et al., 2002). Protein concentrations were determined by A280 measurements using molar absorption coefficients calculated for each protein (Pace, C. N. et al., 1995). Gel filtration chromatography of the purified $V_H$s was performed on a SUPERDEX™ 75 column (GE Healthcare) as described (Deng, S. J. et al., 1995).

Binding and refolding efficiency experiments. Equilibrium dissociation constants ($K_D$ s) and refolding efficiencies (REs) of $V_H$s/$V_H$Hs were derived from surface plasmon resonance (SPR) data collected with a system for real-time biomolecular interaction analysis using surface plasmon resonance (SPR) technology, such as a BIACORE™ 3000 biosensor system (Biacore Inc., Piscataway, NJ). To measure the binding of $V_H$s to protein A, 2000 resonance units (RUs) of protein A or a reference antigen-binding fragment (Fab) were immobilized on research grade CM5 sensor chips (Biacore Inc.). Immobilizations were carried out at concentrations of 25 µg/ml (protein A) or 50 µg/ml (Fab) in 10 mM sodium acetate buffer pH 4.5, using the amine coupling kit provided by the manufacturer. To measure the binding of the anti-idiotypic llama $V_H$Hs to H11 scFv, 4100 RUs of 50

µg/ml H11 scFv or 3000 RUs of 10 µg/ml Se155-4 IgG reference were immobilized as described above. In all instances, analyses were carried out at 25° C. in 10 mM HEPES, pH 7.4, containing 150 mM NaCl, 3 mM EDTA and 0.005% P20 at a flow rate of 40 µl/min, and surfaces were regenerated by washing with the running buffer. To determine the binding activities of the refolded proteins, $V_H$s or $V_H$Hs were denatured by incubation at 85° C. for 20 min at 10 µg/ml concentrations. The protein samples were then cooled down to room temperature for 30 min to refold and were subsequently centrifuged in a microfuge at 14,000 rpm for 5 min at room temperature to remove any protein precipitates. The supernatants were recovered and analyzed for binding activity by SPR as described above. For both folded and refolded proteins data were fit to a 1:1 interaction model simultaneously using BIAevaluation 4.1 software (Biacore Inc.) and $K_D$s were subsequently determined. REs were determined from $$RE = \frac{K_D n}{K_D ref} \times 100$$

Where $K_D$n is the IC, of the native protein and $K_D$ref is the IC, of the refolded protein.

Tryptic digest experiments. 3:1 of a freshly prepared 0.1:g/:l sequencing grade trypsin (Hoffmann-La Roche Ltd., Mississauga, ON, Canada) in 1 mM HCl was added to 60 µg $V_H$ in 100 mM TRIS™—HCl (Tris (hydroxymethyl) aminomethane hydrochloride) buffer pH 7.8. Digestion reactions were carried out in a total volume of 60:1 for 1 h at 37° C. and stopped by adding 5 µl of 0.1:g/:l trypsin inhibitor (Sigma, Oakville, ON, Canada). Following completion of digestion, 5:1 was removed and analyzed by SDS-PAGE; the remaining was desalted using ZIPTIP™$_{C4}$ (pipette tips with chromatography media, 0.6 µL C4 resin, fixed at the end) (Millipore, Nepean, ON, Canada), eluted with 1% acetic acid in 50:50 methanol:water and subjected to $V_H$ mass determination by MALDI mass spectrometry.

Protein stability studies at 37° C. Single-domain antibodies (sdAbs) at 0.32-3.2 mg/ml concentrations were incubated at 37° C. in PBS buffer for 17 days. Following incubation, the protein samples were spun down in a microfuge at maximum speed for 5 min even in the absence of any visible aggregate formation. The samples were then applied onto a SUPERDEX™ 75 size exclusion column (GE Healthcare) and the monomeric peaks were collected for SPR analysis against protein A. SPR analyses were performed as described above except that 500 RUs of protein A or reference Fab was immobilized and that immobilizations were carried out at concentration of 50 µg/ml.

NMR experiments—$V_H$ samples for NMR analysis were dissolved in 10 mM sodium phosphate, 150 mM NaCl, 0.5 mM EDTA, and 0.02% NaN$_3$ at pH 7.0. The protein concentrations were 40 µM-1.0 mM. All NMR experiments were carried out at 298 K on a Bruker AVANCE™-800 or a Bruker AVANCE™-500 NMR spectrometer. One-dimensional (1D) $^1$H NMR spectra were recorded with 16,384 data points and the spectral widths were 8,992.81 Hz at 500 MHz and 17,605.63 Hz at 800 MHz, respectively. Two-dimensional $^1$H-$^1$H NOESY spectra of 2,048×400 data points were acquired on a Bruker AVANCE™-800 NMR spectrometer with a spectral width of 11,990.04 Hz and a mixing time of 120 ms. In all NMR experiments, water suppression was achieved using the WATERGATE method implemented through the 3-9-19 pulse train (Piotto, M. et al., 1992; Sklenar, V. et al., 1993). NMR data were processed and analyzed using the Bruker XWINNMR software package. All PFG-NMR diffusion measurements were carried out with the water-suppressed LED sequence (Altieri, A. S. et al., 1995), on a Bruker AVANCE™-500 NMR spectrometer equipped with a triple-resonance probe with three-axis gradients. One-dimensional proton spectra were processed and analyzed using Bruker Xwinnmr software package. NMR signal intensities were obtained by integrating NMR spectra in the methyl and methylene proton region (2.3 ppm to −0.3 ppm) where all NMR signals were attenuated uniformly at all given PFG strengths.

Human $V_L$ phage display library construction and panning. cDNAs were synthesized from human spleen mRNA as described above for the human $V_H$s. The cDNA was used as template in PCR to amplify $V_L$ genes in 50 µl reaction volumes using six $V_\kappa$ back primers, 11 $V_\lambda$ back primers (de Haard, H. J. et al., 1999), four $V_\kappa$ For primers and two $V_\lambda$ For primers (Sblattero, D. et al., 1998). The back and forward primers were modified to have flanking Apa LI and Not I restriction sites, respectively, for subsequent cloning purposes. Forward primers were pooled together in ratios which reflected their degree of degeneracy. $V_\lambda$ genes were PCRed in 11 separate reactions using the pooled $V_\lambda$ For primers and 11 individual $V_\lambda$ back primers. Similarly, $V_\lambda$ genes were amplified in 6 separate reactions using the pooled $V_\kappa$ For primers and 6 individual $V_\lambda$ back primers. The PCR products were pooled, gel purified and digested with Apa LI and Not I restriction endonucleases. The library was constructed as described for human $V_H$s. Plaque PCR was performed on individual library colonies and the amplified $V_L$ genes were sequenced as described (Tanha, J. et al., 2003). Panning against protein L (Biolynx Inc., Brockville, ON, Canada) and germline sequence assignment of the selected $V_L$s were performed as described above for human $V_H$ library.

$V_L$ expression and purification. $V_L$ expression, purification, concentration determination and gel filtration chromatography were carried out as described for $V_H$s in "$V_H$ expression and purification.".

Expression and purification of $V_L$ and $V_H$ pentamers. Specific primers were used in a standard PCR to amplify HVHP328 $V_H$ and HVLP335 $V_L$ genes. Standard cloning techniques were used to clone the HVHP328 and HVLP335 genes in fusion with VT1B pentamerization domain gene in an expression vector to yield HVHP328PVT2 and HVLP335PTV2 pentamers, (Zhang, J. et al., 2004). Pentamers were expressed and purified as described (Zhang, J. et al., 2004). Protein concentrations were determined as above.

Surface plasmon resonance of $V_L$s. The binding kinetics for the interaction of the $V_L$s to protein L were determined by SPR using BIACORE™ 3000 biosensor system (Biacore, Inc., Piscataway, NJ). 680 RUs of protein L or 870 RUs of a Fab reference were immobilized on research grade CM5 sensor chips (Biacore). Immobilizations were carried out at a protein concentration of 50 µg/ml in 10 mM acetate buffer pH 4.5 using the amine coupling kit supplied by the manufacturer. All measurements were carried out at 25° C. in 10 mM HEPES buffer pH 7.4, containing 150 mM NaCl, 3 mM EDTA and 0.005% P20 at a flow rate of 50 µl/min or 100 µl/min. Surfaces were regenerated by washing with the running buffer. Data were evaluated using the BIAevaluation 4.1 software (Biacore, Inc.).

Surface plasmon resonance of the pentameric $V_L$ and $V_H$. The binding kinetics for the interaction of HVHP328PVT2 with protein A and HVLP335PTV2 with protein L were also determined by SPR. 520 RUs of protein A or a Fab reference were immobilized as above. For the $V_L$ pentamer, the same surfaces prepared above were used. Measurements were carried out as above but at a flow rate of 20 μl/min. Surfaces were regenerated by washing with 50 mM HCl for 3 s. Data were evaluated as described for the monomers.

Cell Microagglutination

A single *S. aureus* colony from a BHI plate was used to inoculate 15 mL of BHI media. The bacteria were grown overnight at 37° C. at 200 rpm. In the morning, the culture was spun down in a swinging bucket, Sorvall RT6000B refrigerated centrifuge at 4000 rpm for 10 min, the supernatant was removed and the cell pellet was re-suspended in PBS buffer. The cells were re-spun, the supernatant was removed and the cell pellet was re-suspended again in PBS buffer. The cells were diluted to an A600 of 1.0, and serial dilutions of the cells were spread on BHI plates at 37° C. for overnight growth. The cell titer was determined in the morning. An A600 of 1.0 corresponded to $1.5 \times 10^9$ cells ml$^{-1}$. Identical steps were taken to prepare *E. coli* starin TG1 cells for subsequent microagglutination assays, except that the growth media was 2xYT. The viable counts were similar, A6001.0=$2.1 \times 10^9$ cells ml$^{-1}$.

To perform microagglutination assays, two fold dilutions of HVHP328PVT2 in PBS were performed from wells 1 to 11 in a microtiter plate. Well 12 (blank) had only PBS. The total volume in each well was 50 μl. Subsequently, $1 \times 10^8$ *S. aureus* cells in 50 μl PBS was added to all wells and the plate was incubated overnight at 4° C. To have a permanent record of the results, a picture was taken from the plate in the morning. For the pentamer control experiment, HVHP328PVT2 was replaced with the $V_L$ pentamer, HVLP335PTV2. In the cell control experiments, the same two sets of experiments were repeated with *E. coli* TG1 cells.

Identification and Sequence Analysis of Monomeric Human $V_L$s

Essentially the same selection method which was employed to isolate soluble $V_H$s from a human $V_H$ phage display library was applied to a human $V_L$ library for isolating soluble, monomeric $V_L$S. A human $V_L$ library with a size of $3 \times 10^6$ was constructed. Twenty four plaques from the library titer plates were picked and their $V_L$ genes were PCRed and sequenced. The sequences were diverse in terms of germ-line origin although 75% of the $V_L$s were of Vλ origin (data not shown). Three rounds of panning against protein L resulted in enrichment for large plaques. Thirty-nine of large plaques were sequenced and 32 unique sequences were identified (FIG. 6). HVLP325, HVLP335 and HVLP351 occurred at frequency of 3, 4 and 2, respectively. Except for HVLP389 which is of lambda class (subgroup Vλ1, germline 1 b), the remaining 31 $V_L$s belonged to the Vκ class. Of the 31 kappa $V_L$s, 24 fall within the VκIII subgroup and 7 within the Vκ1 subgroup. Sixteen of the 24 VκIII sequences utilize L6 germline sequence with the remaining utilizing A27, L2 and L6 germline sequences. The $V_κ1$ subgroup $V_L$s are originated from O2/O12 or A30 germline sequence. Noticeable mutations occurred at position 96. The germline amino acids at this position are aromatic and hydrophobic amino acids Trp, Phe, Tyr, Leu or Ile for kappa $V_L$s and Tyr, Val or Ala for lambda $V_L$s. But in the selected pool of kappa $V_L$s only 5 out of 31 have their germline amino acids at position 96: HVLP325, HVLP349, HVLP388, HVLP3109 and HVLP393. 21 amino acids at position 96 are charged of which 20 are positively-charged: Arg, Lys or His. Two amino acids are Pro, one Gln, one Ser and one Thr. Of seven kappa $V_L$s analyzed by gel filtration chromatography for monomericity, six which had Arg or Lys at position 96 were also monomers, whereas HVLP325 with the germline amino acid Leu at position 96 formed aggregates (see below). Similarly, HVLP389 which was of the lambda class and had a germline mutation to Ser was also monomeric (see below). These data correlates the deviation from the germline amino acids at position 96 (27 out of 32) with improved biophysical properties of $V_L$s such as monomericity.

Eighteen $V_L$s of the kappa class had their last three residues (105-107) replaced with amino acids Thr, Val and Leu which are only found in lambda $V_L$s. These substitutions may have had a role in improving the biophysical properties of the kappa $V_L$s, resulting in the selection of the aforementioned $V_L$s over the parental clones with the original kappa residues at position 105-107.

Characterization of the Human $V_L$s

Eight of the selected $V_L$s with different V germline origins were expressed in *E. coli* in one-liter cultures and purified: HVLP324, HVLP325, HVLP335, HVLP342, HVLP351, HVLP364, HVLP389 and HVLP3103 (Table 6). All were expressed in good yields ranging from 6.2 mg for HVLP324 to around 75 mg for HVLP335 and HVLP364.

The aggregation tendency of the human $V_L$s was assessed in terms of their oligomerization state by gel filtration chromatography. $V_L$s were subjected to SUPERDEX™ 75 gel filtration chromatography at a concentration of 0.6 mg/ml. All except HVLP325 were essentially free of aggregates and gave symmetric single peaks with the mean apparent molecular mass of 12.7 kDa (range, 6.2-19.2 kDa) (FIG. 7A and Table 3). This is in agreement with the expected molecular mass for monomeric $V_L$s, 13.4-13.8 kDa. Variation in apparent molecular mass for single-domain antibodies has been reported previously (Jespers, L. et al., 2004a; (Stevens, F. J. et al., 1980). For HVLP325, the aggregates formed 11% of the total protein (aggregate plus monomer). HVLP351, HVLP342, HVLP335 and HVLP3103, were still monomer when tested at their highest concentration available, i.e., 0.89 mg/ml, 1.0 mg/ml, 4.9 mg/ml and 5.9 mg/ml, respectively (FIG. 7B)

$V_L$s were subjected to SUPERDEX™-75 chromatography prior to BIACORE™ analysis and purified monomer peaks collected even in the absence of any evidence of aggregated material. In SPR analysis, all selected $V_L$s bound to protein L (FIG. 8). This was not unexpected since the $V_L$s were isolated by panning against protein L. For all, the $K_D$s of binding to protein L were in 0.6-3 μM (Table 3). HVLP324 and HVLP342 had additional smaller $K_D$s, 10 nM and 40 nM, respectively. Low affinity and high affinity bindings of $V_L$s of Vκl subgroup to protein L have been reported previously (Reference). Both, HVLP324 and HVLP342, belong to Vκl subgroup (Table 3). As expected, the kinetic and equilibrium data were consistent with the monomeric peak being indeed monomeric.

Binding Analyses of Pentamers

Bindings of HVHP328PVT2 pentamer to protein A and HVLP335PTV2 pentamer to protein L were determined by surface plasmon resonance (FIG. 9). The association rates were independently calculated from plots of $k_{obs}$ versus concentration. More than one dissociation rate ($k_d$) could be calculated due to the heterogeneity in multivalent binding amongst the pentamer population. Therefore, more than one equilibrium dissociation constant, $K_D$, could be obtained. HVHP328PTV2 and HVLP335PTV2 had minimum $K_D$s of 2 nM and 200 μM, respectively (Table 4). With slower $k_d$s, HVHP328PTV2 and HVLP335PTV2 had $K_D$S as low as 900 and 90 pM, respectively.

Pathogen Detection by $V_L$s and $V_H$s

The protein A and L binding activity of the $V_H$s and $V_L$s can be used to detect bacteria which have protein A and/or L on their surfaces. This is possible if the $V_H$s and $V_L$s are soluble and monomeric (lack of tendency to aggregate) such as the $V_H$s and $V_L$s here. Variable domains derived from antibodies which lack light chains such as camelid heavy chain antibodies or nurse shark and wobbegong shark IgNARs are naturally soluble and monomeric. From these, those with protein A and L binding activity can also be used to detect bacteria which have protein A and/or L on their surfaces. Protein A is present on the surface of the pathogenic bacteria, Staphylococcus aureus. Thus, the $V_H$s with protein A binding activity such as the ones described here can be used to detect S. aureus. We performed a microagglutination assay to detect the ability of HVHP328PVT2 $V_H$ pentamer to bind to S. aureus. A constant number of bacterial cells were incubated with two-fold dilutions of HVHP328PVT2 in microtiter wells (wells 1-11) (FIG. 10). Well 12 had buffer instead of the pentamer. If the $V_H$s bind to the bacterial cells, then the pentamer because of its multimeric nature should be able to cross-link the cells and results in cell agglutination. The agglutinated cells will appear as diffused cells in a microtiter well (FIG. 10). In the absence of any binding, no agglutination should occur, hence no agglutination, and the cells will appear as a dot at the bottom of the well. As shown in FIG. 10, the pentamer binds to the S. aureus, since there is agglutination of cells. The agglutination is observed up to well 7. Beyond well 7 the concentration of the pentamer is too low for binding, hence no agglutination. The control $V_L$ pentamer does not show any agglutination, demonstrating the specificity of the $V_H$ pentamer to S. aureus (FIG. 10). The binding is also cell-specific since the $V_H$ pentamer as expected does not agglutinate E. coli (TG1 strain) or Salmonella cells (data not shown). Similarly, the $V_L$ monomers and $V_L$ pentamers with protein L binding activity can be used for the detection of bacteria, in particular pathogenic bacteria such as Peptostreptococcus magnus, which have protein L on their cells surface.

It is understood that the examples described above in no way serve to limit the true scope of this invention, but rather are presented for illustrative purposes.

REFERENCE LIST

Bai, Y. and Feng, H. (2004). Selection of stably folded proteins by phage-display with proteolysis. Eur. J. Biochem. 271: 1609-1614.

Davies, J. and Riechmann, L (Feb. 21, 1994). 'Camelising' human antibody fragments: NMR studies on VH domains. FEBS Lett 339: 285-290.

Davies, J. and Riechmann, L (1995). Antibody VH domains as small recognition units. Biotechnology N. Y. 13: 475-479.

de Haard, H. J., van Neer, N., Reurs, A., Hufton, S. E., Roovers, R. C., Henderikx, P., de Bruine, A. P., Arends, J. W., and Hoogenboom, H. R. (Jun. 25, 1999). A large non-immunized human Fab fragment phage library that permits rapid isolation and kinetic analysis of high affinity antibodies. J. Biol. Chem. 274: 18218-18230.

Deng, S. J., MacKenzie, C. R., Hirama, T., Brousseau, R., Lowary, T. L., Young, N. M., Bundle, D. R., and Narang, S. A. (May 23, 1995). Basis for selection of improved carbohydrate-binding single-chain antibodies from synthetic gene libraries. Proc. Natl. Acad. Sci U. S. A 92: 4992-4996.

Forrer, P., Jung, S., and Pluckthun, A. (1999). Beyond binding: using phage display to select for structure, folding and enzymatic activity in proteins. Curr. Opin. Struct. Biol. 9: 514-520.

Fournier, B. and Klier, A. (2004). Protein A gene expression is regulated by DNA supercoiling which is modified by the ArlS-ArlR two-component system of Staphylococcus aureus. Microbiology 150: 3807-3819.

Hamers, C. C., Atarhouch, T., Muyldermans, S., Robinson, G., Hamers, C., Songa, E. B., Bendahman, N., and Hamers, R. (Jun. 3, 1993). Naturally occurring antibodies devoid of light chains. Nature 363: 446-448.

Jespers, L., Schon, O., Famm, K., and Winter, G. (2004a). Aggregation-resistant domain antibodies selected on phage by heat denaturation. Nat. Biotechnol. 22: 1161-1165.

Jespers, L., Schon, O., James, L. C., Veprintsev, D., and Winter, G. (Apr. 2, 2004b). Crystal Structure of HEL4, a Soluble, Refoldable Human V(H) Single Domain with a Germ-line Scaffold. J. Mol. Biol. 337: 893-903.

Jung, S., Honegger, A., and Pluckthun, A. (Nov. 19, 1999). Selection for improved protein stability by phage display. J. Mol. Biol. 294: 163-180.

Matsuura, T. and Pluckthun, A. (Mar. 27, 2003). Selection based on the folding properties of proteins with ribosome display. FEBS Lett. 539: 24-28.

Muruganandam, A., Tanha, J., Narang, S., and Stanimirovic, D. (2002). Selection of phage-displayed llama single-domain antibodies that transmigrate across human blood-brain barrier endothelium. FASEB J. 16: 240-242.

Pace, C. N., Vajdos, F., Fee, L., Grimsley, G., and Gray, T. (1995). How to measure and predict the molar absorption coefficient of a protein. Protein Sci. 4: 2411-2423.

Ricci, S., Medaglini, D., Marcotte, H., Olsen, A., Pozzi, G., and Bjorck, L. (2001). Immunoglobulin-binding domains of peptostreptococcal protein L enhance vaginal colonization of mice by Streptococcus gordonii. Microb. Pathog. 30: 229-235.

Sambrook, J. F. E. F. a. M. T. (1989). "Molecular Cloning: A laboratory Manual ($2^{nd}$ ed.)", Cold Spring Harbor Laboratory, Cold Spring Harbor, NY Sblattero, D. and Bradbury, A. (1998). A definitive set of oligonucleotide primers for amplifying human V regions. Immunotechnology. 3: 271-278.

Tanha, J., Dubuc, G., Hirama, T., Narang, S. A., and MacKenzie, C. R. (May 1, 2002). Selection by phage display of llama conventional V(H) fragments with heavy chain antibody V(H)H properties. J. Immunol. Methods 263: 97-109.

Tanha, J., Muruganandam, A., and Stanimirovic, D. (2003). Phage Display Technology for Identifying Specific Antigens on Brain Endothelial Cells. Methods Mol. Med. 89: 435-450.

Tanha, J., Xu, P., Chen, Z. G., Ni, F., Kaplan, H., Narang, S. A., and MacKenzie, C. R. (Jul. 6, 2001). Optimal design features of camelized human single-domain antibody libraries. J. Biol. Chem 276: 24774-24780.

van der Linden, R. H., Frenken, L. G., de Geus, B., Harmsen, M. M., Ruuls, R. C., Stok, W., de Ron, L., Wilson, S., Davis, P., and Verrips, C. T. (Apr. 12, 1999). Comparison of physical chemical properties of llama VHH antibody fragments and mouse monoclonal antibodies. Biochim Biophys. Acta 1431: 37-46.

Waldo, G. S. (2003). Genetic screens and directed evolution for protein solubility. Curr. Opin. Chem. Biol. 7: 33-38.

Ward, E. S., Gussow, D., Griffiths, A. D., Jones, P. T., and Winter, G. (Oct. 12, 1989). Binding activities of a repertoire of single immunoglobulin variable domains secreted from *Escherichia coli* [see comments]. Nature 341: 544-546.

Zhang, J., Li, Q., Nguyen, T. D., Tremblay, T. L., Stone, E., To, R., Kelly, J., and MacKenzie, C. R. (Jul. 30, 2004). A pentavalent single-domain antibody approach to tumor antigen discovery and the development of novel proteomics reagents. J. Mol. Biol. 341: 161-169.

TABLE 1

$V_H$ sequence deviations from parental germline sequences

| VH | V/J germlines | Amino acid deviation from V and FR4 germline sequences |
|---|---|---|
| HVHP44 | DP47/JH4b | L5V, Q105R |
| HVHB82 | DP47/JH6c | E1Q, L5Q |
| HVHP421 | DP47/JH4b | E1Q, V2L, L5Q, L11V, G16R |
| HVHP419 | DP47/JH4b | E1Q, V2L, L5Q, T77S, R83G, K94R |
| HVHP430 | DP47/JH3b | E1Q, L5V, V12I, Q13K, S31N, G52AS, L78V, A93V, K94R |
| HVHP429 | DP47/JH4 | L5V, G10T, S30I, S31N, G42D, E46D, A50T, G52aN, S53N, S56A K75N, A84P, E85D |
| HVHM41 | DP47/JH3a | E1Q, L5V, E6Q, G16R, T28A, S53G, G55D, S56H, M108L |
| HVHM81 | DP47JH3a | L5V, E6Q, G16R, S30D, S31D, S35H, A50G, G55A, E85G, V89L, K94R |
| HVHP428 | V3-49/JH4b | E1Q, V2L, V5Q, R16G, T23A, G30S, D31S, T60A, G73D, K83R, T84A, V89M, T93A |
| HVHP420 | DP-38/JH4b | E1Q, S35T, S52aT |
| HVHP414 | DP-38/JH3b | E1D, E6Q, A23T, T28P, K52T, A60V |
| HVHP423 | V3-53/JH1 | E1Q, V2M, E6Q, L11V, I12V, N32S, Y33R, V37F, K43M, K64R, T68S, V89L |
| HVHP44B | V3-53/JH1 | E1Q, E6Q, N32S, Y33R, V37F, K43M, Y58S, K64R, T68S, V89L |
| HVHP413 | YAC-5/JH3b | E1Q, E6Q, Q13K, V29F, S31D, N32Y, V50F |
| HVHP426 | 8-1B/JH3b | E1Q, E6Q, L11V, G16R, T28I, S30D, S31G, N32Y, Y33A, S35H, K43Q, I51T, Y52N, S53N, Y58S, L78V |

TABLE 2

Biophysical characteristics of the human $V_H$s

| $V_H/V_HH$ | Exp.# (mg) | $K_D$ (μM) | Trypsin resistance | RE (%) |
|---|---|---|---|---|
| HVHP44 | 8.2 | 1.3 | √ | 93 |
| HVHB82 | 5.9 | 0.2 | √ | 71 |
| HVHP421 | 5.5 | 1.0 | √ | 14 |

TABLE 2-continued

Biophysical characteristics of the human $V_H$s

| $V_H/V_HH$ | Exp.# (mg) | $K_D$ (μM) | Trypsin resistance | RE (%) |
|---|---|---|---|---|
| HVHP419 | 3.4 | 1.6 | √ | 84 |
| HVHP430 | 6.4, 23.7 | 2.3 | √ | 88 |
| HVHP429 | 3.4 | 1.3 | √ | 86 |
| HVHM41 | 1.8 | 0.5 | X | 92 |
| HVHM81 | 4.3 | 1.3 | √ | 87 |
| HVHP428 | 3.1 | 1.8 | √ | 95 |
| HVHP420 | 59.0 | 1.2 | √ | 92 |
| HVHP414 | 11.8 | 1.6 | √ | 73 |
| HVHP423 | 2.4, 62.1 | 3.0 | √ | 86 |
| HVHP413 | 5.8 | 0.3 | √ | 52 |
| HVHP426 | 6.3 | 0.8 | √ | 70 |
| H11F9* | ND | 3.5 | ND | 95 |
| H11B2* | ND | 2.0 | ND | 100 | expression yield per liter of bacterial culture
*$K_D$s and REs were determined against H11 scFv.

TABLE 3

Characteristics of the human $V_L$s

| VL | Subgroup | Expression[a] mg | $K_D$ μM | Oligomerization state[b] |
|---|---|---|---|---|
| HVLP324 | VκI | 6.9 | 0.2, 0.01[c] | Monomer |
| HVLP325 | VκIII | 6.2 | 1 | Monomer/Aggregate |
| HVLP335 | VκIII | 73.5 | 2 | Monomer |
| HVLP342 | VκI | 7.7 | 0.6, 0.04[c] | Monomer |
| HVLP351 | VκIII | 8.9 | 2 | Monomer |
| HVLP364 | VκIII | 77.1 | 3 | Monomer |
| HVLP389 | VλI | 16.7 | 1 | Monomer |
| HVLP3103 | VκIII | 19.0 | 1 | Monomer |

[a]Expression yield per liter of bacterial culture.
[b]Oligomerization state was determined by gel filtration chromatography.
[c]The smaller KD values correspond to the binding of the of HVLP324 and HVLP342 to the high affinity sites on protein L.

TABLE 4

Kinetic and equilibrium constants for the bindings of HVHP328PTV2 and HVLP335PTV2 to protein A and L, respectively

| Pentabody | HVHP328PTV2 | HVLP335PTV2 |
|---|---|---|
| $k_a$ (M$^{-1}$s$^{-1}$) | $4.3 \times 10^5$ | $1.7 \times 10^6$ |
| $k_d$ (s$^{-1}$) | $<1 \times 10^{-3}$ | $<4 \times 10^{-4}$ |
| $K_D$ (M) | $<2 \times 10^{-9}$ | $<2 \times 10^{-10}$ |

The invention claimed is:

1. An antigen-binding $V_L$ comprising a FR1 sequence of EIVMTQSPGTLSLSPGDRATLSC (amino acids 1-23 of SEQ ID NO:42), a FR2 sequence of WYQQKPGQAPRLLIY (amino acids 35-49 of SEQ ID NO:42), a FR3 sequence of GIPDRFSGSGSGTDFTLTISR-LEPEDFAVYYC (amino acids 57-88 of SEQ ID NO:42), and a FR4 sequence of FGQGTKVTVL (amino acids 98-107 of SEQ ID NO:42).

2. An antigen-binding $V_L$ comprising the FR1, FR2, FR3, and FR4 portion of SEQ ID NO:42 and one or more randomized CDR sequences, wherein one or more of CDR1, CDR2 and CDR3 of SEQ ID NO:42 is replaced, respectively, with a randomized CDR1, CDR2 and CDR3.

3. The antigen-binding $V_L$ of claim 1, wherein the $V_L$ is in a multimeric form.

4. The antigen-binding $V_L$ of claim 1, wherein the $V_L$ is in a dimeric form.

5. The antigen-binding $V_L$ of claim 1, wherein $V_L$ is in a trimeric form.

6. The antigen-binding $V_L$ of claim 1, wherein the $V_L$ is in a pentameric form.

7. A display library constructed by preparing nucleic acid sequences coding for the antigen-binding $V_L$ of claim 1 or 2 and expressing the $V_L$ so as to display the antigen-binding $V_L$ sequence of claim 1 or 2.

8. The display library of claim 7, wherein the library is a phage display library.

9. The display library of claim 7, wherein the library is a ribosome display, ARM ribosome display, yeast display, bacterial cell display, or in vitro compartmentalization library.

10. A method for producing a $V_L$ library, comprising:
   a) providing a nucleotide sequence encoding the antigen-binding $V_L$ of claim 1;
   b) providing oligonucleotide sequences with randomized codons;
   c) incorporating the randomized oligonucleotides into the nucleotide sequence encoding the $V_L$, such that one or more than one of the complementary determining regions is randomized, wherein one or more of CDR1, CDR2 and CDR3 of SEQ ID NO.: 42 is replaced, respectively, with a randomized CDR1, CDR2 and CDR3;
   d) expressing the nucleotide sequences produced in step c); and
   e) screening the expressed sequences for binding to a target polypeptide.

11. The method of claim 10, wherein the screening comprises panning against a target molecule.

12. A method of screening the display library of claim 7, comprising panning the displayed $V_L$ against a target molecule.

13. The antigen-binding $V_L$ of claim 2, wherein CDR3 of SEQ ID NO:42 is replaced with a randomized CDR3, and the randomized CDR3 comprises 9 amino acid residues.

14. The antigen-binding $V_L$ of claim 1, which is aggregation resistant.

\* \* \* \* \*

SEQUENCE LISTING

<160> NUMBER OF SEQ ID NOS: 55

<210> SEQ ID NO 1
<211> LENGTH: 122
<212> TYPE: PRT
<213> ORGANISM: Homo sapiens

<400> SEQUENCE: 1

Glu Val Gln Leu Val Glu Ser Gly Gly Gly Leu Ile Gln Pro Gly Gly
1               5                   10                  15

Ser Leu Arg Leu Ser Cys Ser Ala Ser Gly Phe Ile Val Ser Ser Asp
            20                  25                  30

Tyr Met Asn Trp Val Arg Gln Ala Pro Gly Arg Gly Leu Glu Trp Val

```
            35                  40                  45
Ser Val Ile Asn Ser Asp Gly Ser Thr Lys Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Asp Leu Ala Tyr Cys Gly His Cys Asp His Ser Pro Trp
                100                 105                 110

Gly Gln Gly Thr Met Val Thr Val Ser Ser
            115                 120
```

<210> SEQ ID NO 2
<211> LENGTH: 124
<212> TYPE: PRT
<213> ORGANISM: Homo sapiens

<400> SEQUENCE: 2

```
Gln Val Gln Leu Val Gln Ser Gly Gly Gly Leu Val Lys Ser Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Thr Tyr Tyr Asp Ile Leu Thr Gly Pro Thr Asn Gly Met Asp
                100                 105                 110

Val Trp Gly Gln Gly Thr Leu Val Thr Val Ser Ser
            115                 120
```

<210> SEQ ID NO 3
<211> LENGTH: 113
<212> TYPE: PRT
<213> ORGANISM: Homo sapiens

<400> SEQUENCE: 3

```
Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Thr Asp Met Glu Val Trp Gly Lys Gly Thr Thr Val Thr Val Ser
                100                 105                 110

Ser
```

<210> SEQ ID NO 4
<211> LENGTH: 118
<212> TYPE: PRT
<213> ORGANISM: Homo sapiens

<400> SEQUENCE: 4

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Arg Asn Thr
65                  70                  75                  80

Ile Tyr Leu Gln Met Asn Ser Leu Lys Thr Glu Asp Thr Ala Met Tyr
                85                  90                  95

Tyr Cys Thr Thr Asp Leu Thr Gln Trp Ala Ala Trp Gly Gln Gly Thr
            100                 105                 110

Met Val Thr Val Ser Ser
        115
```

<210> SEQ ID NO 5
<211> LENGTH: 118
<212> TYPE: PRT
<213> ORGANISM: Homo sapiens

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Asn Met Asn Trp Val Arg Gln Ala Pro Gly Lys Gly Leu Glu Trp Val
        35                  40                  45

Ser Tyr Ile Gly Ile Ser Tyr Asn Thr His Tyr Ala Asp Ser Val Lys
    50                  55                  60

Gly Arg Phe Thr Ile Ser Arg Asp His Ala Lys Asn Ser Leu Tyr Leu
65                  70                  75                  80

Gln Met Asn Ser Leu Arg Asp Glu Asp Thr Ala Val Tyr Tyr Cys Ala
                85                  90                  95

Arg Glu Ala Ser Gly Arg Asp Asp Phe Asp Ile Trp Gly Gln Gly Thr
            100                 105                 110

Met Val Thr Val Ser Ser
        115
```

<210> SEQ ID NO 6
<211> LENGTH: 119
<212> TYPE: PRT
<213> ORGANISM: Homo sapiens

<400> SEQUENCE: 6

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Val Trp Val
         35                  40                  45

Ser Arg Ile Lys Ser Asp Gly Ser Ser Thr Ser Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Glu Lys Ser Leu Glu Leu Pro Asp Asp Tyr Trp Gly Gln Gly
             100                 105                 110

Thr Leu Val Thr Val Ser Ser
        115

<210> SEQ ID NO 7
<211> LENGTH: 116
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ile Ile His Gly Gly Gly Asn Thr Tyr Tyr Ala Asp Ser Val Lys
 50                      55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Glu Tyr Ser Gly Ala Phe Asp Ile Trp Gly Gln Gly Thr Met Val
             100                 105                 110

Thr Val Ser Ser
        115

<210> SEQ ID NO 8
<211> LENGTH: 124
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Glu Pro Arg Ser Val Ser Gly Leu Arg Gly Val Val Asp
             100                 105                 110
```

```
Ser Trp Gly Arg Gly Thr Leu Val Thr Val Ser Ser
        115                 120
```

<210> SEQ ID NO 9
<211> LENGTH: 113
<212> TYPE: PRT
<213> ORGANISM: Homo sapiens

<400> SEQUENCE: 9

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Thr Asp Met Glu Val Trp Gly Lys Gly Thr Val Thr Val Ser Ser
            100                 105                 110
```

<210> SEQ ID NO 10
<211> LENGTH: 123
<212> TYPE: PRT
<213> ORGANISM: Homo sapiens

<400> SEQUENCE: 10

```
Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Lys Gly Gly Ser Gly Tyr Asp His Pro Asp Tyr
            100                 105                 110

Trp Gly Gln Gly Thr Leu Val Thr Val Ser Ser
        115                 120
```

<210> SEQ ID NO 11
<211> LENGTH: 122
<212> TYPE: PRT
<213> ORGANISM: Homo sapiens

<400> SEQUENCE: 11

```
Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Ser Leu Tyr
 65                  70                  75                  80
Leu Gln Met Asn Ser Leu Gly Ala Glu Asp Thr Ala Val Tyr Tyr Cys
                 85                  90                  95
Ala Arg Ser Trp Ser Gly Ser Ser Tyr Gly Gly Asp Leu Asp Ser Trp
                100                 105                 110
Gly Gln Gly Thr Leu Val Thr Val Ser Ser
                115                 120
```

<210> SEQ ID NO 12
<211> LENGTH: 125
<212> TYPE: PRT
<213> ORGANISM: Homo sapiens

<400> SEQUENCE: 12

```
Gln Val Gln Leu Val Glu Ser Gly Gly Gly Leu Ile Lys Pro Gly Gly
 1               5                  10                  15
Ser Leu Arg Leu Ser Cys Ala Ala Ser Gly Phe Thr Phe Ser Asn Tyr
                 20                  25                  30
Ala Met Ser Trp Val Arg Gln Ala Pro Gly Lys Gly Leu Glu Trp Val
             35                  40                  45
Ser Ala Ile Ser Ser Ser Gly Gly Ser Thr Tyr Tyr Ala Asp Ser Val
         50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Ala Val Tyr Tyr Cys
                 85                  90                  95
Val Arg Glu Glu Tyr Arg Cys Ser Gly Thr Ser Cys Pro Gly Ala Phe
                100                 105                 110
Asp Ile Trp Gly Gln Gly Thr Met Val Thr Val Ser Ser
                115                 120                 125
```

<210> SEQ ID NO 13
<211> LENGTH: 119
<212> TYPE: PRT
<213> ORGANISM: Homo sapiens

<400> SEQUENCE: 13

```
Glu Val Gln Leu Val Glu Ser Gly Gly Thr Leu Val Gln Pro Gly Gly
 1               5                  10                  15
Ser Leu Arg Leu Ser Cys Ala Ala Ser Gly Phe Thr Phe Ile Asn Tyr
                 20                  25                  30
Ala Met Ser Trp Val Arg Gln Ala Pro Asp Lys Gly Leu Asp Trp Val
             35                  40                  45
Ser Thr Ile Ser Asn Asn Gly Gly Ala Thr Tyr Tyr Ala Asp Ser Val
         50                  55                  60
Lys Gly Arg Phe Thr Ile Ser Arg Asp Asn Ser Asn Asn Thr Leu Tyr
 65                  70                  75                  80
Leu Gln Met Asn Ser Leu Arg Pro Asp Asp Thr Ala Val Tyr Tyr Cys
                 85                  90                  95
Ala Lys Gly Pro Ile Asn Thr Gly Arg Tyr Gly Asp Trp Gly Gln Gly
                100                 105                 110
Thr Leu Val Thr Val Ser Ser
```

-continued

```
               115

<210> SEQ ID NO 14
<211> LENGTH: 123
<212> TYPE: PRT
<213> ORGANISM: Homo sapiens

<400> SEQUENCE: 14

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Ala Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Met Val Arg Gly Val Ser Ser Ala Pro Phe Asp Tyr
            100                 105                 110

Trp Gly Gln Gly Thr Leu Val Thr Val Ser Ser
        115                 120

<210> SEQ ID NO 15
<211> LENGTH: 121
<212> TYPE: PRT
<213> ORGANISM: Homo sapiens

<400> SEQUENCE: 15

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Leu Tyr Tyr Cys
                85                  90                  95

Ala Arg Gln Ser Ile Thr Gly Pro Thr Gly Ala Phe Asp Val Trp Gly
            100                 105                 110

Gln Gly Thr Met Val Thr Val Ser Ser
        115                 120

<210> SEQ ID NO 16
<211> LENGTH: 123
<212> TYPE: PRT
<213> ORGANISM: Homo sapiens

<400> SEQUENCE: 16

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Arg Ala Glu Asp Thr Ala Met Tyr
                85                  90                  95

Tyr Cys Ala Arg Arg Ala Lys Asp Gly Tyr Asn Ser Pro Glu Asp Tyr
            100                 105                 110

Trp Gly Gln Gly Thr Leu Val Thr Val Ser Ser
            115                 120
```

<210> SEQ ID NO 17
<211> LENGTH: 119
<212> TYPE: PRT
<213> ORGANISM: Homo sapiens

<400> SEQUENCE: 17

```
Gln Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Gly Arg Ile Lys Thr Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Asp Arg Asp His Ser Ser Gly Ser Trp Gly Gln Gly
            100                 105                 110

Thr Leu Val Thr Val Ser Ser
        115
```

<210> SEQ ID NO 18
<211> LENGTH: 119
<212> TYPE: PRT
<213> ORGANISM: Homo sapiens

<400> SEQUENCE: 18

```
Asp Val Gln Leu Val Gln Ser Gly Gly Gly Leu Val Lys Pro Gly Gly
 1               5                   10                  15

Ser Leu Arg Leu Ser Cys Thr Ala Ser Gly Phe Pro Phe Ser Asn Ala
            20                  25                  30

Trp Met Ser Trp Val Arg Gln Ala Pro Gly Lys Gly Leu Glu Trp Val
        35                  40                  45

Gly Arg Ile Thr Ser Lys Thr Asp Gly Gly Thr Thr Asp Tyr Val Ala
    50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Asp Gln Ala Asn Ala Phe Asp Ile Trp Gly Gln Gly
            100                 105                 110
```

Thr Met Val Thr Val Ser Ser
            115

<210> SEQ ID NO 19
<211> LENGTH: 118
<212> TYPE: PRT
<213> ORGANISM: Homo sapiens

<400> SEQUENCE: 19

Gln Met Gln Leu Val Gln Ser Gly Gly Gly Val Val Gln Pro Gly Gly
1               5                   10                  15

Ser Leu Arg Leu Ser Cys Ala Ala Ser Gly Phe Thr Val Ser Ser Ser
            20                  25                  30

Arg Met Ser Trp Phe Arg Gln Ala Pro Gly Met Gly Leu Glu Trp Val
        35                  40                  45

Ser Val Ile Tyr Ser Gly Gly Ser Thr Tyr Tyr Ala Asp Ser Val Arg
    50                  55                  60

Gly Arg Phe Ser Ile Ser Arg Asp Asn Ser Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Arg Glu Arg Glu Gly Ala Val Thr Arg Glu Asp Trp Gly Gln Gly Thr
            100                 105                 110

Leu Val Thr Val Ser Ser
            115

<210> SEQ ID NO 20
<211> LENGTH: 118
<212> TYPE: PRT
<213> ORGANISM: Homo sapiens

<400> SEQUENCE: 20

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Ser
            20                  25                  30

Arg Met Ser Trp Phe Arg Gln Ala Pro Gly Met Gly Leu Glu Trp Val
        35                  40                  45

Ser Val Ile Tyr Ser Gly Gly Ser Thr Ser Tyr Ala Asp Ser Val Arg
    50                  55                  60

Gly Arg Phe Ser Ile Ser Arg Asp Asn Ser Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Arg Glu Arg Glu Gly Ala Val Thr Arg Glu Asp Trp Gly Gln Gly Thr
            100                 105                 110

Leu Val Thr Val Ser Ser
            115

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Gly Gly Leu Val Lys Pro Gly Gly
1               5                   10                  15

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Phe Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Arg Val Gly Gly Gly Ala Phe Asp Ile Trp Gly Gln Gly
            100                 105                 110

Thr Met Val Thr Val Ser Ser
            115
```

`<210> SEQ ID NO 22`
`<211> LENGTH: 120`
`<212> TYPE: PRT`
`<213> ORGANISM: Homo sapiens`

`<400> SEQUENCE: 22`

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ile Val Asp Gly Tyr
            20                  25                  30

Ala Met His Trp Val Arg Gln Ala Pro Gly Gln Gly Leu Glu Trp Val
        35                  40                  45

Ser Val Thr Asn Asn Gly Gly Ser Thr Ser Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Ser Ile Thr Gly Pro Thr Gly Ala Phe Asp Ile Trp Gly Gln
            100                 105                 110

Gly Thr Met Val Thr Val Ser Ser
            115                 120
```

`<210> SEQ ID NO 23`
`<211> LENGTH: 107`
`<212> TYPE: PRT`
`<213> ORGANISM: Homo sapiens`

`<400> SEQUENCE: 23`

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Ser Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Cys Cys Gln Gln Tyr Gly Ser Ser Pro Arg
                85                  90                  95
```

-continued

Thr Phe Gly Gln Gly Thr Lys Val Thr Val Leu
            100                 105

<210> SEQ ID NO 24
<211> LENGTH: 107
<212> TYPE: PRT
<213> ORGANISM: Homo sapiens

<400> SEQUENCE: 24

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Ser Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Val Thr Val Leu
            100                 105

<210> SEQ ID NO 25
<211> LENGTH: 107
<212> TYPE: PRT
<213> ORGANISM: Homo sapiens

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Homo sapiens

<400> SEQUENCE: 26

Glu Ile Val Leu Thr Gln Ser Pro Ala Thr Leu Ser Leu Ser Pro Gly
1               5                   10                  15

Gln Arg Ala Thr Leu Ser Cys Arg Ala Ser Arg Ser Val Gly Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
            50                  55                  60
Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Ser Ser Pro Lys
                 85                  90                  95

Thr Phe Gly Gln Gly Thr Lys Val Thr Val Leu
            100                 105
```

<210> SEQ ID NO 27
<211> LENGTH: 107
<212> TYPE: PRT
<213> ORGANISM: Homo sapiens

<400> SEQUENCE: 27

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
         50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Ser Ser Pro Lys
                 85                  90                  95

Thr Phe Gly Gln Gly Thr Lys Val Thr Val Leu
            100                 105
```

<210> SEQ ID NO 28
<211> LENGTH: 107
<212> TYPE: PRT
<213> ORGANISM: Homo sapiens

<400> SEQUENCE: 28

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Arg Ser Val Ser Tyr His
                 20                  25                  30

Leu Ala Trp Tyr Gln Gln Lys Pro Gly Gln Ala Pro Lys Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Thr Val Leu
            100                 105
```

<210> SEQ ID NO 29
<211> LENGTH: 107
<212> TYPE: PRT
<213> ORGANISM: Homo sapiens

<400> SEQUENCE: 29

```
Glu Ile Val Met Thr Gln Ser Pro Ala Thr Leu Ser Leu Ser Pro Gly
  1               5                  10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Ile Tyr Tyr Cys Gln Gln Arg Ser Gly Trp Pro Lys
                85                  90                  95

Thr Phe Gly Gln Gly Thr Lys Val Thr Val Leu
            100                 105
```

<210> SEQ ID NO 30
<211> LENGTH: 106
<212> TYPE: PRT
<213> ORGANISM: Homo sapiens

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln His Tyr Gly Thr Ser Lys Thr
                85                  90                  95

Phe Gly Arg Gly Thr Lys Val Thr Val Leu
            100                 105
```

<210> SEQ ID NO 31
<211> LENGTH: 107
<212> TYPE: PRT
<213> ORGANISM: Homo sapiens

<400> SEQUENCE: 31

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Thr Phe Gly Gly Gly Thr Lys Val Glu Ile Lys
            100                 105
```

<210> SEQ ID NO 32

<211> LENGTH: 106
<212> TYPE: PRT
<213> ORGANISM: Homo sapiens

<400> SEQUENCE: 32

Glu Ile Val Leu Thr Gln Ser Pro Thr Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Arg Pro Gly Gln Ala Pro Arg Leu Leu Val
        35                  40                  45

Phe Asp Thr Ser Asn Arg Ala Pro Gly Val Pro Ala Arg Phe Ser Gly
50                  55                  60

Arg Gly Ser Gly Thr Leu Phe Thr Leu Thr Ile Ser Ser Leu Glu Pro
65                  70                  75                  80

Glu Asp Ser Ala Val Tyr Phe Cys Gln Gln Arg Ser Ser Gly Leu Thr
                85                  90                  95

Phe Gly Gly Gly Thr Lys Val Thr Val Leu
            100                 105

<210> SEQ ID NO 33
<211> LENGTH: 106
<212> TYPE: PRT
<213> ORGANISM: Homo sapiens

<400> SEQUENCE: 33

Glu Ile Val Met Thr Gln Ser Pro Gly Thr Leu Ser Leu Ser Pro Gly
1               5                   10                  15

Gly Arg Ala Thr Leu Ser Cys Arg Ala Ser Gln Ser Val Ser Ser His
            20                  25                  30

Leu Ala Trp Tyr Gln Gln Lys Pro Gly Gln Thr Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Gly Ile Tyr Tyr Cys Gln Gln Arg Ser Asn Arg Leu Ser
                85                  90                  95

Phe Gly Gly Gly Thr Lys Val Thr Val Leu
            100                 105

<210> SEQ ID NO 34
<211> LENGTH: 107
<212> TYPE: PRT
<213> ORGANISM: Homo sapiens

<400> SEQUENCE: 34

Glu Ile Val Met Thr Gln Ser Pro Val Thr Leu Ser Leu Ser Pro Gly
1               5                   10                  15

Glu Arg Ala Thr Leu Ser Cys Arg Ala Ser Gln Ser Val Gly Thr Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Ser Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Pro Arg
                85                  90                  95

Thr Phe Gly Gly Gly Thr Lys Val Thr Val Leu
            100                 105

<210> SEQ ID NO 35
<211> LENGTH: 107
<212> TYPE: PRT
<213> ORGANISM: Homo sapiens

<400> SEQUENCE: 35

Glu Ile Val Met Thr Gln Ser Pro Ala Thr Leu Pro Leu Ser Pro Gly
1               5                   10                  15

Glu Arg Ala Thr Leu Ser Cys Arg Ala Ser Gln Ser Val Ser Ser His
            20                  25                  30

Leu Ala Trp Tyr Gln Gln Lys Pro Gly Gln Ala Pro Arg Leu Leu Ile
        35                  40                  45

Tyr Asp Ala Ser His Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Tyr Trp Pro Leu
                85                  90                  95

Thr Phe Gly Gly Gly Thr Lys Val Thr Val Leu
            100                 105

<210> SEQ ID NO 36
<211> LENGTH: 107
<212> TYPE: PRT
<213> ORGANISM: Homo sapiens

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Gly Ser
            20                  25                  30

Leu Ala Trp Tyr Gln Gln Thr Pro Gly Gln Ala Pro Arg Leu Leu Ile
        35                  40                  45

Tyr Gly Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ser Ala Val Tyr Tyr Cys Gln Gln Arg Gly Asp Trp Pro Ser
                85                  90                  95

Thr Phe Gly Gly Gly Thr Lys Val Thr Val Leu
            100                 105

<210> SEQ ID NO 37
<211> LENGTH: 106
<212> TYPE: PRT
<213> ORGANISM: Homo sapiens

<400> SEQUENCE: 37

Glu Ile Val Leu Thr Gln Ser Pro Thr Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Arg Pro Gly Gln Ala Pro Arg Leu Leu Val

```
                35                  40                  45
Phe Asp Thr Ser Asn Arg Ala Pro Gly Val Pro Ala Arg Phe Ser Gly
 50                  55                  60

Arg Gly Ser Gly Thr Leu Phe Thr Leu Thr Ile Ser Ser Leu Glu Pro
 65                  70                  75                  80

Glu Asp Ser Ala Val Tyr Phe Cys Gln Lys Arg Ser Ser Gly Leu Thr
                 85                  90                  95

Phe Gly Gly Gly Thr Lys Val Thr Val Leu
                100                 105

<210> SEQ ID NO 38
<211> LENGTH: 109
<212> TYPE: PRT
<213> ORGANISM: Homo sapiens

<400> SEQUENCE: 38

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Gly Arg Ser
                 20                  25                  30

Leu Val Trp Tyr Gln His Lys Pro Gly Gln Ala Pro Arg Leu Leu Ile
                 35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro His
                 85                  90                  95

Met Tyr Thr Phe Gly Gln Gly Thr Lys Val Glu Ile Lys
                100                 105

<210> SEQ ID NO 39
<211> LENGTH: 105
<212> TYPE: PRT
<213> ORGANISM: Homo sapiens

<400> SEQUENCE: 39

Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Ser Leu Ala Trp Tyr Gln Gln Lys Pro Gly Gln Ala Pro Arg Leu Leu
                 35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Gly
 65                  70                  75                  80

Pro Glu Asp Val Ala Val Tyr Tyr Cys Gln Gln Ser Pro Glu Thr Phe
                 85                  90                  95

Gly Gln Gly Thr Lys Val Glu Ile Lys
                100                 105

<210> SEQ ID NO 40
<211> LENGTH: 108
<212> TYPE: PRT
<213> ORGANISM: Homo sapiens

<400> SEQUENCE: 40
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr His Phe Thr Leu Thr Ile Asn Arg Leu Glu
65                  70                  75                  80

Pro Gly Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
                100                 105
```

<210> SEQ ID NO 41
<211> LENGTH: 107
<212> TYPE: PRT
<213> ORGANISM: Homo sapiens

<400> SEQUENCE: 41

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Asn
            20                  25                  30

Val Ala Trp Phe Gln Gln Lys Pro Gly Gln Pro Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Glu Thr Asp Phe Thr Leu Thr Ile Ser Arg Leu Glu Pro
65                  70                  75                  80

Glu Asp Phe Ala Val Tyr Tyr Cys Arg Gln Tyr Asp Lys Ser Pro Lys
                85                  90                  95

Thr Phe Gly Gln Gly Thr Lys Val Asp Ile Lys
                100                 105
```

<210> SEQ ID NO 42
<211> LENGTH: 107
<212> TYPE: PRT
<213> ORGANISM: Homo sapiens

<400> SEQUENCE: 42

```
Glu Ile Val Met Thr Gln Ser Pro Gly Thr Leu Ser Leu Ser Pro Gly
1               5                   10                  15

Asp Arg Ala Thr Leu Ser Cys Arg Ala Ser Gln Asp Ile Ser Thr Tyr
            20                  25                  30

Leu Ala Trp Tyr Gln Gln Lys Pro Gly Gln Ala Pro Arg Leu Leu Ile
        35                  40                  45

Tyr Ser Ala Ser Arg Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ser Ser Ser Pro Lys
                85                  90                  95

Thr Phe Gly Gln Gly Thr Lys Val Thr Val Leu
                100                 105
```

<210> SEQ ID NO 43
<211> LENGTH: 107
<212> TYPE: PRT
<213> ORGANISM: Homo sapiens

<400> SEQUENCE: 43

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Lys Asn
            20                  25                  30

Leu Ala Trp Tyr Gln Lys Lys Pro Gly Gln Ser Pro Arg Leu Leu Ile
        35                  40                  45

His Ser Ile Ser Thr Arg Ala Thr Gly Val Pro Ala Arg Phe Ser Gly
    50                  55                  60

Gly Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Asn Ser Pro Gln
                85                  90                  95

Thr Phe Gly Gln Gly Thr Lys Val Glu Ile Lys
            100                 105

<210> SEQ ID NO 44
<211> LENGTH: 107
<212> TYPE: PRT
<213> ORGANISM: Homo sapiens

<400> SEQUENCE: 44

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Asn Asn
            20                  25                  30

Leu Ala Trp Tyr Gln Gln Arg Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Val
65                  70                  75                  80

Glu Asp Val Ala Val Tyr Tyr Cys Gln Gln Tyr Tyr Thr Thr Pro Lys
                85                  90                  95

Thr Phe Gly Gln Gly Thr Lys Val Glu Ile Lys
            100                 105

<210> SEQ ID NO 45
<211> LENGTH: 107
<212> TYPE: PRT
<213> ORGANISM: Homo sapiens

<400> SEQUENCE: 45

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

```
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro His
                 85                  90                  95

Ser Ser Gly Gln Gly Thr Lys Val Glu Ile Lys
            100                 105
```

<210> SEQ ID NO 46
<211> LENGTH: 107
<212> TYPE: PRT
<213> ORGANISM: Homo sapiens

<400> SEQUENCE: 46

```
Glu Thr Thr Leu Thr Gln Ser Pro Ala Thr Leu Ser Val Ser Pro Gly
  1               5                  10                  15

Glu Arg Ala Thr Phe Ser Cys Arg Ala Ser Gln Ser Val Ser Asn Asn
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Thr Thr Gly Ile Pro Asp Arg Phe Ser Ala
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Asp Thr Ser Pro Arg
                 85                  90                  95

Thr Phe Gly Gln Gly Thr Lys Val Glu Ile Lys
            100                 105
```

<210> SEQ ID NO 47
<211> LENGTH: 107
<212> TYPE: PRT
<213> ORGANISM: Homo sapiens

<400> SEQUENCE: 47

```
Asp Ile Gln Leu Thr Gln Ser Pro Ser Ser Leu Ser Ala Ser Val Gly
  1               5                  10                  15

Asp Arg Val Thr Ile Thr Cys Arg Ala Ser Gln Ser Ile Ser Thr Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Glu Ser Gly Val Pro Ser Arg Phe Ser Gly
 50                  55                  60

Arg Gly Ser Gly Thr Asp Phe Thr Leu Thr Val Ser Ser Leu Gln Pro
 65                  70                  75                  80

Glu Asp Phe Ala Thr Tyr Phe Cys Gln Gln Gly Tyr Thr Thr Pro Arg
                 85                  90                  95

Thr Phe Gly Gln Gly Thr Lys Val Thr Val Leu
            100                 105
```

<210> SEQ ID NO 48
<211> LENGTH: 107
<212> TYPE: PRT
<213> ORGANISM: Homo sapiens

<400> SEQUENCE: 48

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Thr Tyr
```

```
                    20                  25                  30
Leu Asn Trp Tyr Gln Gln Lys Pro Gly Lys Ala Pro Lys Leu Leu Ile
            35                  40                  45

Phe Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Thr Val Leu
            100                 105

<210> SEQ ID NO 49
<211> LENGTH: 107
<212> TYPE: PRT
<213> ORGANISM: Homo sapiens

<400> SEQUENCE: 49

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Phe Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Pro Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Thr Val Pro
            100                 105

<210> SEQ ID NO 51
<211> LENGTH: 107
<212> TYPE: PRT
```

<213> ORGANISM: Homo sapiens

<400> SEQUENCE: 51

Asp Ile Gln Met Thr Gln Ser Pro Pro Ser Leu Ser Ala Phe Val Gly
1               5                   10                  15

Asp Arg Val Thr Ile Thr Cys Arg Ala Ser Glu Ser Val Gly Asn Ser
            20                  25                  30

Leu Ser Trp Tyr Gln Leu Lys Pro Gly Lys Asn Pro Arg Leu Leu Val
        35                  40                  45

Ser Gly Gly Ser Phe Leu Gln Ser Gly Val Ser Ala Arg Phe Ser Gly
    50                  55                  60

Ser Gly Ala Gly Thr Leu Phe Thr Leu Thr Ile Thr Gly Leu Arg Leu
65                  70                  75                  80

Asp Asp Ser Ala Thr Tyr Tyr Cys Gln Gln Ser Asp Ala Val Pro Arg
                85                  90                  95

Thr Phe Gly His Gly Thr Lys Val Ser Val Leu
            100                 105

<210> SEQ ID NO 52
<211> LENGTH: 107
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Thr Asp
            20                  25                  30

Leu Asp Trp Phe Gln Gln Arg Pro Gly Arg Ala Pro His Arg Leu Ile
        35                  40                  45

Tyr Gly Ala Ser Ser Leu Gln Gly Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His His Thr Tyr Pro Arg
                85                  90                  95

Thr Phe Gly Leu Gly Thr Lys Val Thr Val Leu
            100                 105

<210> SEQ ID NO 53
<211> LENGTH: 107
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Met Ala Pro Lys Arg Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

```
Thr Phe Gly Gln Gly Thr Lys Val Thr Val Leu
            100                 105

<210> SEQ ID NO 54
<211> LENGTH: 110
<212> TYPE: PRT
<213> ORGANISM: Homo sapiens

<400> SEQUENCE: 54

Gln Ser Val Val Thr Gln Pro Pro Ser Val Ser Ala Ala Pro Gly Gln
1               5                   10                  15

Arg Val Thr Ile Ser Cys Ser Gly Ser Ser Tyr Asn Ile Gly Glu Asn
            20                  25                  30

Ser Val Ser Trp Tyr Gln Gln Leu Pro Gly Thr Ala Pro Lys Leu Leu
        35                  40                  45

Ile Tyr Gly Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Asn Leu
                85                  90                  95

Arg Ala Ser Val Phe Gly Gly Gly Thr Lys Val Thr Val Leu
            100                 105                 110

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5
```